(12) United States Patent
Muñoz-Torrero López-Ibarra et al.

(10) Patent No.: US 9,238,626 B2
(45) Date of Patent: Jan. 19, 2016

(54) BETA-AMYLOID-DIRECTED MULTITARGET COMPOUNDS FOR THE TREATMENT OF ALZHEIMER'S DISEASE

(71) Applicants: UNIVERSITAT DE BARCELONA, Barcelona (ES); PONTIFICIA UNIVERSIDAD CATÓLICA DE CHILE, Santiago de Chile (CL)

(72) Inventors: Diego Muñoz-Torrero López-Ibarra, Viladecans (ES); Nibaldo Manuel Inestrosa Cantín, Santiago de Chile (CL); Elisabet Viayna Gaza, Alella (ES); Irene Sola Lao, Terrassa (ES); Santiago Vázquez Cruz, Cornellà de Llobregat (ES)

(73) Assignees: UNIVERSITAT DE BARCELONA, Barcelona (ES); PONTIFICIA UNIVERSIDAD CATÓLICA DE CHILE, Santiago (CL)

( * ) Notice: Subject to any disclaimer, the term of this patent is extended or adjusted under 35 U.S.C. 154(b) by 0 days.

(21) Appl. No.: 14/400,314
(22) PCT Filed: May 9, 2013
(86) PCT No.: PCT/EP2013/059683
§ 371 (c)(1),
(2) Date: Nov. 10, 2014
(87) PCT Pub. No.: WO2013/167711
PCT Pub. Date: Nov. 14, 2013

(65) Prior Publication Data
US 2015/0099776 A1 Apr. 9, 2015

(30) Foreign Application Priority Data
May 10, 2012 (ES) .................................. 201230706

(51) Int. Cl.
C07D 221/22 (2006.01)
C07D 221/18 (2006.01)
A61K 31/439 (2006.01)

(52) U.S. Cl.
CPC ............ C07D 221/22 (2013.01); C07D 221/18 (2013.01)

(58) Field of Classification Search
CPC ... C07D 221/18; C07D 221/22; A61K 31/439
USPC ................................ 514/284, 289; 546/61, 74
See application file for complete search history.

(56) References Cited

U.S. PATENT DOCUMENTS 5,965,569 A * 10/1999 Camps Garcia et al. ..... 514/289

FOREIGN PATENT DOCUMENTS

WO WO2007122274 A1 11/2007
WO WO2011076969 A1 6/2011

OTHER PUBLICATIONS

Camps; J. Med. Chem. 2005, 48, 1701-1704.*
(Continued)

*Primary Examiner* — Janet L Andres
*Assistant Examiner* — Daniel Carcanague
(74) *Attorney, Agent, or Firm* — Peter B. Scull; Hamilton, DeSanctis & Cha, LLP

(57) ABSTRACT

The compounds of formula (I), or its pharmaceutically acceptable salts, or any stereoisomer or mixture thereof, wherein: $R_1$ is a ($C_1$-$C_2$) alkyl radical; $R_2$ and $R_3$ are radicals independently selected from the group consisting of F, Cl and methyl $R_4$ is H or OH; A is a birradical selected from the group consisting of —$(CH_2)_n$— and —$(CH_2)$-phenyl-$(CH_2)$—; t is an integer from 0 to 1; and n is an integer from 8 to 15, are useful for the treatment of Alzheimer's disease.

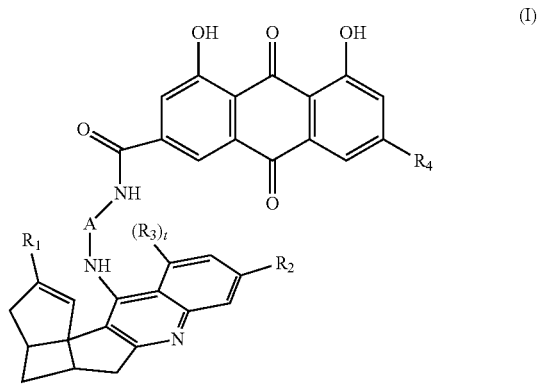

15 Claims, 9 Drawing Sheets

(56) References Cited

OTHER PUBLICATIONS

Martinez; Expert Opin. Investig. Drugs, 2006, 15, 1-12.*
Jung; Bioorganic and Medicinal Chemistry Letters, 2007, 17, 1082-1090.*
Ronco; Bioorganic and Medicinal Chemistry, 2009, 17, 4523-4536.*
Ronco; Eur. J. Org. Chem., 2011, 302-310.*
Camps; J. Med. Chem. 2008, 51, 3588-3598.*
Carles Galdeano et al, "Huprine-Tacrine Heterodimers as Anti-Amyloidogenic Compounds of Potential Interest Against Alzheimer's and Prion Diseases", Journal of Medicinal Chemistry, vol. 55, No. 2, Jan. 26, 2012, pp. 661-669, XP055077717, ACS Publication, Washington DC.
Muñoz-Torrero et al, "Dimeric and Hybrid Anti-Alzheimer Drug Candidates", Current Medicinal Chemistry, vol. 13, Jan. 1, 2006, pp. 399-422, XP055077718, Retrieved from the Internet: URL:http://docserver.ingentaconnect.com/deliver/connect/ben/09298673/v13n4/s3.pdf?expires=1378307902&id=75380320&titleid=3863&accname=EuropaeischesPatentamt&checksum=4A4A86A3DA07A5E6C93F09E3C45D4FCA, [retrieved on Sep. 4, 2013], Bentham Science Publishers, Ltd., Sharjah, U.A.E.
Illkay Orhan et al, "Coumarin, Anthroquinone and Stilbene Derivatives with Anticholinesterase Activity", Z. Naturforsch, vol. 63c, Jan. 1, 2008, pp. 366-370, XP05577780, Retrieved from the Internet: URL://www.znaturforsch.com/rc/s63c0366.pdf [retrieved on Sep. 5, 2013; Retrieved by the International Searching Examiner as reflected in the International Search Report cited below], Verlag der Zeitschrift für Naturforschung C, Tübingen, Germany.
Andrea Cavalli et al, "A Small Molecule Targeting the Multifactorial Nature of Alzheimer's Disease", Angewandte. Chemie International Edition, vol. 46, Issue 20, May 11, 2007, pp. 3689-3692, XP002712939, Wiley-VCH Verlag Gmbh & Co. KGaA, Weinheim, Germany.
International Search Report for PCT/EP2013/059683, European Patent Office, mailed Oct. 14, 2013, pp. 1-3, Rijswijk, NL.

* cited by examiner

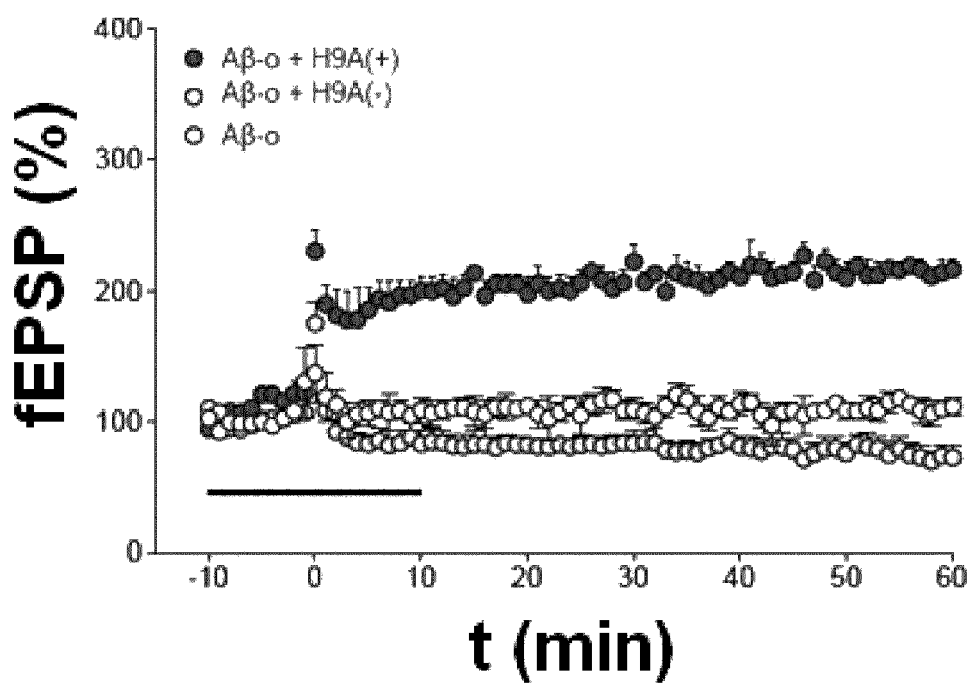
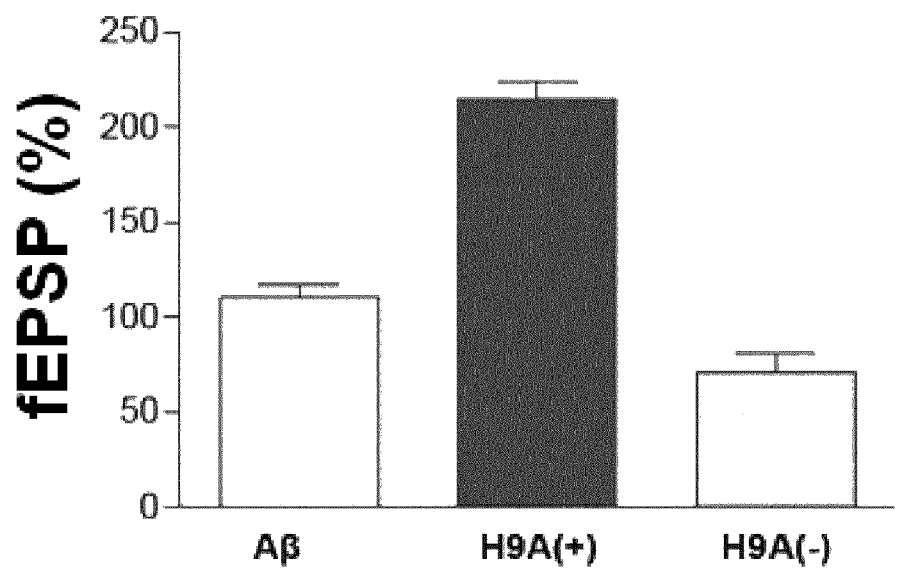
FIG 3

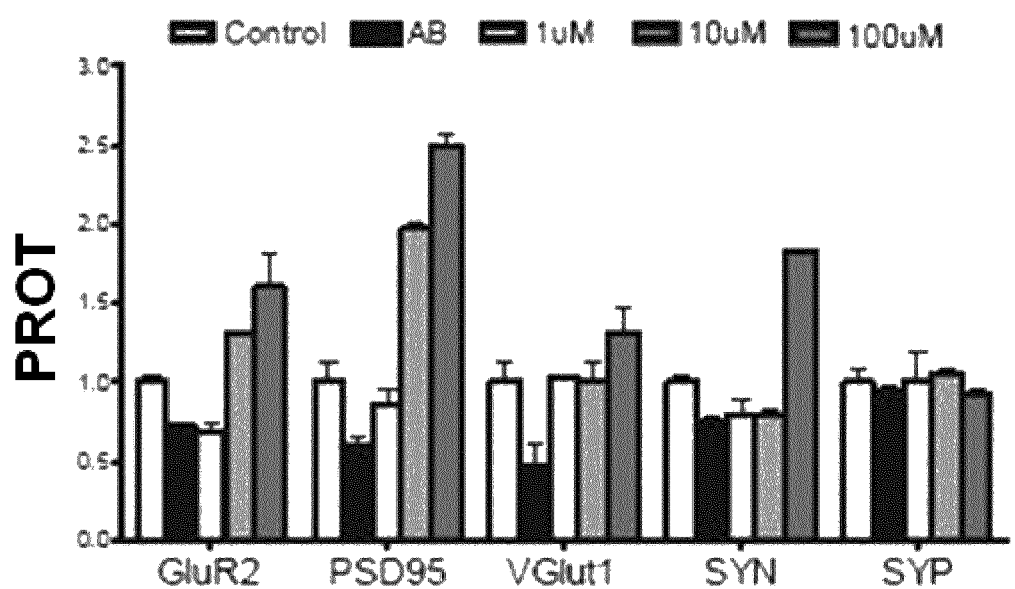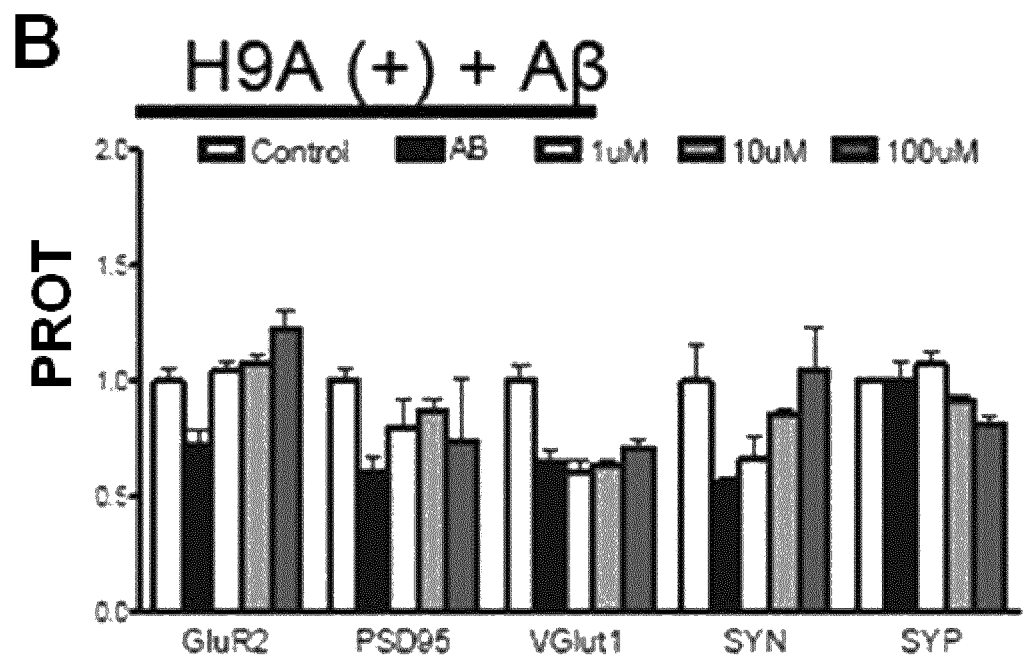
FIG 4

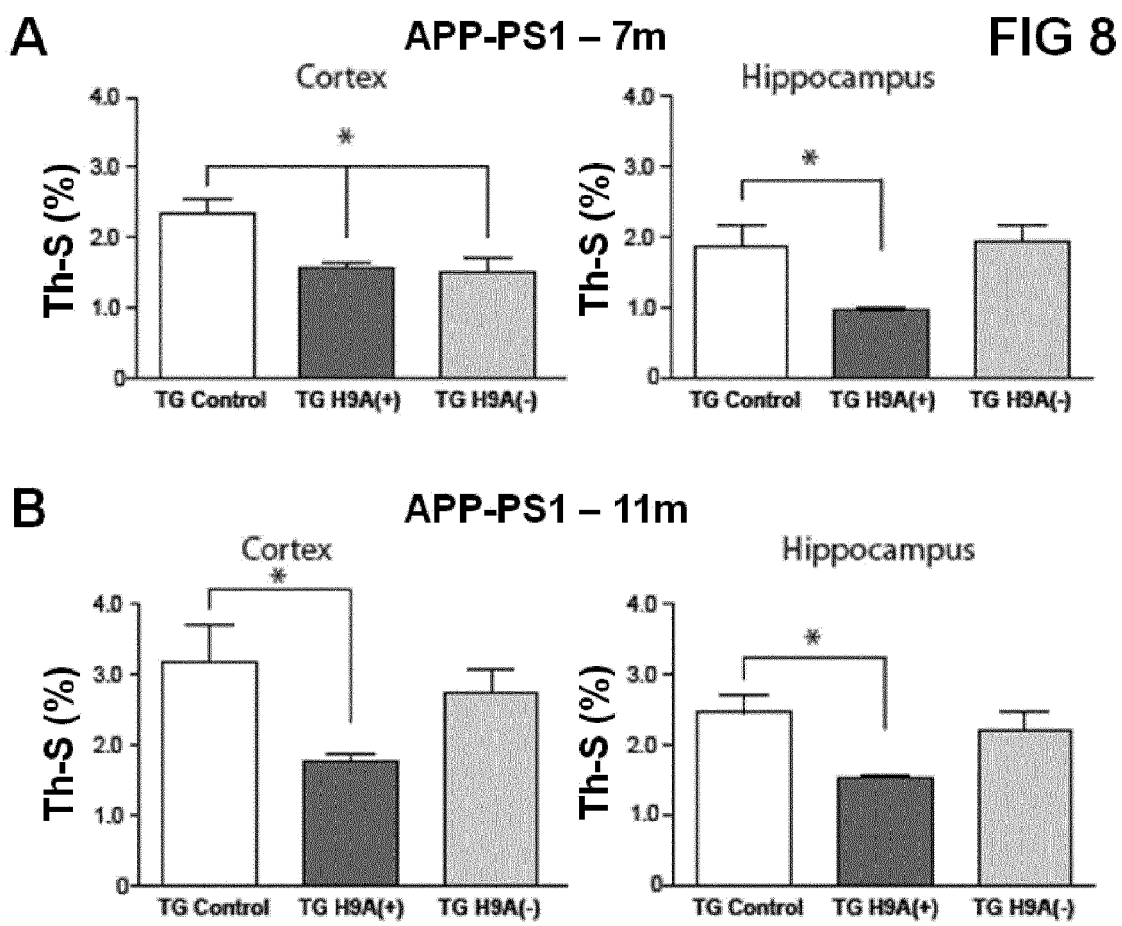

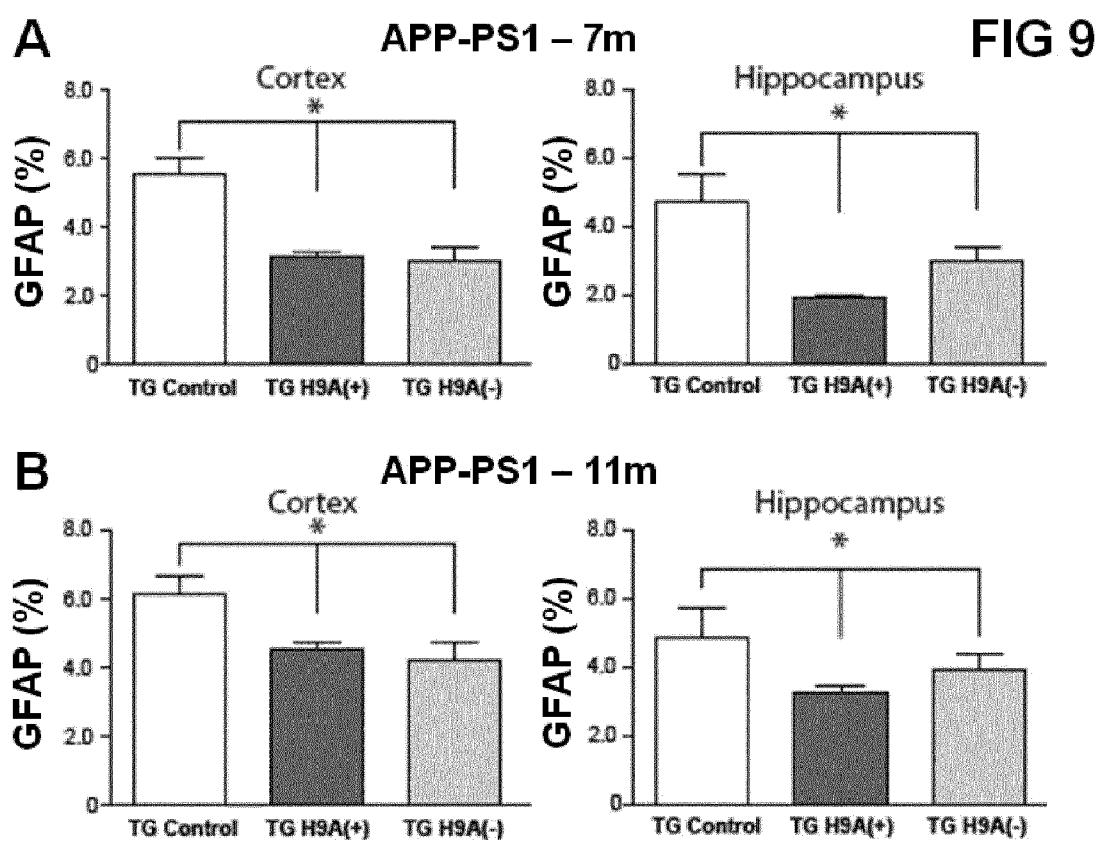

BETA-AMYLOID-DIRECTED MULTITARGET COMPOUNDS FOR THE TREATMENT OF ALZHEIMER'S DISEASE

The invention refers to compounds that are able to modulate at multiple points the underlying mechanisms of the neurodegenerative process of Alzheimer's disease and to a process for their preparation. It also relates to pharmaceutical compositions comprising these compounds and to their use for the treatment of Alzheimer's disease.

BACKGROUND ART

Alzheimer's disease (AD) is a slow, progressive, and ultimately fatal neurodegenerative disorder, clinically characterized by a noticeable cognitive decline defined by a loss of memory and learning ability, together with a reduced ability to perform basic activities of daily living, and a diverse array of neuropsychiatric symptoms. It mainly affects older people. After 65, the likelihood of developing AD doubles every 5 years. Some 35 million people worldwide, i.e. about 0.5% of the world's total population, are suffering dementia, in most cases AD. AD is among the top ten leading causes of death in developed countries, but the only one among them that cannot be cured, prevented or even slowed down. As a consequence of its increasing prevalence and devastating effects, AD is currently affecting every health system in the world. The total worldwide estimated cost associated with AD accounts for approximately 1% of the world's gross domestic product. Worryingly, the figures associated to AD are rising both in terms of mortality and prevalence. Thus, death rates from other major diseases have dropped since 2000, whereas the number of deaths from AD has risen 66%. Also, it is estimated that the prevalence of AD will double every 20 years, reaching 66 million people worldwide by 2030 and 115 million by 2050. Consequently, there is an acute need for effective pharmacotherapies of AD.

Therapeutic interventions currently available for AD, namely the acetylcholinesterase (AChE) inhibitors donepezil, galantamine and rivastigmine and the glutamate NMDA receptor antagonist memantine, are merely symptomatic. These drugs compensate for neurotransmitter deficits that arise at the end of the neurotoxic cascade of AD as a consequence of the neuronal death and are responsible for the cognitive decline of AD patients. In contrast, most drug candidates under clinical development have been designed to hit one of the biological targets involved in the early pathogenic events of the neurotoxic cascade of AD that are responsible for the neuronal death, mainly the formation of the beta-amyloid peptide (Aβ), which involves the proteolysis of the amyloid precursor protein by the sequential action of the enzymes β-secretase (BACE-1) and γ-secretase, and the subsequent aggregation of Aβ into toxic oligomers and fibrils. Disappointingly, the most advanced drug candidates in clinical trials hitting these biological targets have failed in the past years. The clinical development of the Aβ-antiaggregating compound tramiprosate and the γ-secretase modulator tarenflurbil, whose launching was expected by 2009/2010, was discontinued in advanced Phase III trials shortly before these dates due to efficacy issues. Analogously, clinical development of the promising BACE-1 inhibitor LY2811376 was discontinued in Phase I trials in 2011 due to toxicity findings observed in parallel longer-term preclinical studies in mice that are unrelated to BACE-1 inhibition.

Even though BACE-1, γ-secretase and Aβ aggregation, as well as tau aggregation or hyperphosphorylation or oxidative stress, among others, remain viable targets, it seems that they should be hit in a different approach. It is becoming increasingly apparent that diseases, in general, and complex diseases as AD, in particular, are not linear processes but rather complex networks of interconnected protein targets, with alternative, redundant, compensatory signaling pathways that render ineffective the modulation of a single target of the pathological network by compounds as those anti-Alzheimer drug candidates that are recently failing in clinical trials. Conversely, simultaneous modulation of several targets involved in the pathological network should result in a more efficient therapeutic approach. Thus, simultaneous blockade of several important nodes of the pathological network of AD is emerging as a therapeutic approach for efficiently interfering the underlying mechanisms of the disease.

The multitarget approach to AD can be accomplished by means of single compounds that are structurally suited to hit different biological targets.

In vitro inhibitory activities of AChE and AChE-induced Aβ aggregation have been reported for different families of dual binding site AChEIs. The catalytic site of AChE is involved in the hydrolysis of the neurotransmitter acetylcholine, whereas the peripheral site is involved in a binding process with Aβ that accelerates the aggregation of this peptide. Thus, simultaneous blockade of the catalytic and peripheral sites of AChE by dual binding site AChE inhibitors (AChEIs) results in the simultaneous modulation of two important targets of AD pathology, namely Aβ aggregation and the cholinergic deficit. Among the compounds disclosed having in vitro inhibitory activities of AChE and AChE-induced Aβ aggregation are memoquin (cf. e.g. A. Cavalli et al., "A Small Molecule Targeting the Multifunctional Nature of Alzheimer's Disease" *Angew. Chem. Int. Ed.* 2007, vol. 46, pp. 3689-3692) or some hybrid compounds having the 5,6-dimethoxy-2-[(4-piperidinyl)methyl)]-1-indanone moiety of donepezil (or the indane derivative thereof) and a unit of tacrine or huprine as the peripheral to mid-gorge and active site interacting moieties (cf. WO2007122274 or WO2011076969, respectively). There is only one example of dual binding site AChEI in clinical trials for Alzheimer's disease, namely Noscira's NP-61, which entered phase I clinical trials in 2007. For this compound a potent AChE inhibitory activity and Aβ-antiaggregating effect have been reported.

Therefore, despite all the research efforts invested in the past, there is still an important need to find compounds for the treatment of Alzheimer's disease which could modify the course of AD, stopping or slowing down the disease progression.

SUMMARY OF THE INVENTION

Inventors have found novel compounds which reduce synaptic failure, amyloid pathology and cognitive impairment in a well established mouse model of AD, likely through a multitarget mechanism of action which includes the interference with beta-amyloid formation and aggregation. Indeed, in vivo studies with *Escherichia coli* overexpressing Aβ42 have confirmed their ability to inhibit Aβ aggregation. Very interestingly, in another in vivo model of *E. coli* which overexpresses tau protein, these compounds have shown to be able to inhibit tau protein aggregation. Moreover, in vitro these compounds exhibit a high inhibitory activity towards β-secretase (BACE-1), i.e. they are able to block Aβ formation. BACE-1 has been largely investigated as a therapeutic target for disease-modifying agents in AD, since BACE-1 is involved in the first and rate-limiting step of Aβ formation from its protein precursor APP. Because Aβ aggregation is partially a concentration-dependent event, reduction of brain Aβ levels by inhibition of BACE-1 is of utmost importance for a disease-modifying anti-Alzheimer therapeutic approach. In addition, these compounds are also able to hit in vitro other important molecular targets in the neurodegenerative cascade, including AR aggregation, AChE and butyrylcholinesterase (BChE), an enzyme which exerts a compensatory effect in response to a great decrease in brain AChE activity as AD progresses.

Therefore, these compounds have complementary actions arising from hitting a number of distinct biological targets involved in AD neurotoxic cascade. These facts are especially relevant since if administered in an early phase these compounds could stop the neurodegenerative process, i.e. they should be able to interfere upstream in the neurotoxic cascade of AD, and therefore, positively modify AD progression, which makes these compounds very promising disease modifying anti-Alzheimer drugs.

The therapy with a single multimodal drug is advantageous over other polypharmacological approaches based on the use of drug cocktails or fixed dose combinations, where more than one compound are used, because it results in simpler formulation, pharmacokinetics, regulatory barriers, clinical trial design and medication regimens, lack of drug-drug interactions, as well as better patient compliance, which is a critical issue in AD care.

Accordingly, an aspect of the present invention relates to a compound of formula (I) or its pharmaceutically acceptable salts, or any stereoisomer or mixture of stereoisomers, either of the compound of formula (I) or of their salts,

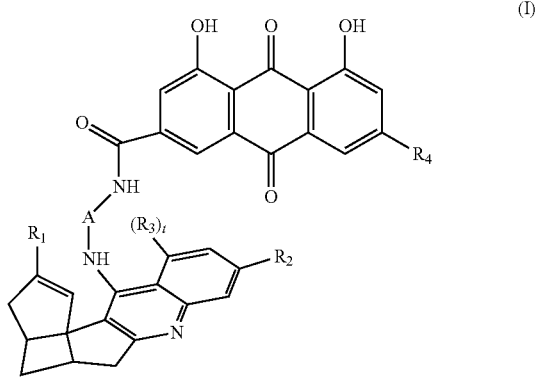

(I)

wherein: $R_1$ is a ($C_1$-$C_2$) alkyl radical; $R_2$ and $R_3$ are radicals independently selected from the group consisting of F, Cl and methyl; $R_4$ is H or OH; A is a birradical selected from the group consisting of —($CH_2$)$_n$— and —($CH_2$)-phenyl-($CH_2$)—; t is an integer from 0 to 1; and n is an integer from 8 to 15.

The new compounds of formula (I) or their salts can exist in solvated, as well as unsolvated forms, including hydrated forms. Thus, they can contain in its structure stoichiometric amounts of solvent in the case of solvates, or of water in the case of hydrates. It is to be understood that the invention encompasses all such solvated, as well as unsolvated forms.

As mentioned above, the pharmaceutically acceptable salts of the compound of formula (I) include acid addition salts such as the hydrochloride, but also any other pharmaceutically acceptable salts of other acids such as hydrobromic, hydrofluoric, sulphuric, phosphoric, acetic, citric, fumaric, gluconic, lactic, maleic, succinic or tartaric acid.

In a preferred embodiment, compounds of formula (I) are those wherein $R_1$ is methyl, $R_2$ is Cl, t is 0, and $R_4$ is H. These compounds have the following formula ($I_i$):

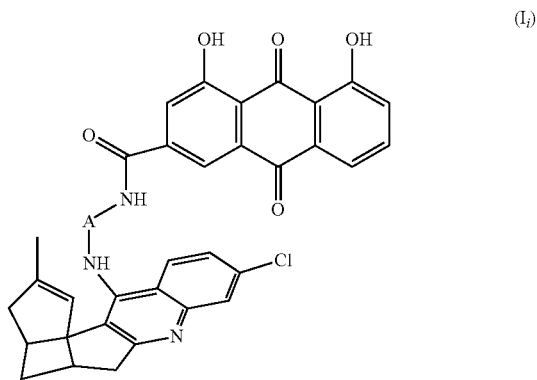

($I_i$)

Preferably, the $CH_2$ groups in —($CH_2$)-phenyl-($CH_2$)— are in para position.

In a more preferred embodiment, compounds of formula (I) are those where A is —($CH_2$)$_n$— and n is an integer from 8 to 12. In a more preferred embodiment, compounds of formula (I) are those where n is an integer from 8 to 9.

In another more preferred embodiment, compounds of formula (I) are those where A is —($CH_2$)-phenyl-($CH_2$)—.

The most preferred compounds of formula (I) are those selected from the following list:

(±)-N-{8-[(3-chloro-6,7,10,11-tetrahydro-9-methyl-7,11-methanocycloocta[b]quinolin-12-yl)amino]octyl}-9,10-dihydro-4,5-dihydroxy-9,10-dioxoanthracene-2-carboxamide ($I_a$);

(±)-N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide ($I_b$);

(−)-(7S,11S)—N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide (−)-($I_b$);

(+)-(7R,11R)—N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide (+)-($I_b$);

(±)-N-{10-[(3-chloro-6,7,10,11-tetrahydro-9-methyl-7,11-methanocycloocta[b]quinolin-12-yl)amino]decyl}-9,10-dihydro-4,5-dihydroxy-9,10-dioxoanthracene-2-carboxamide ($I_c$);

(±)-N-{11-[(3-chloro-6,7,10,11-tetrahydro-9-methyl-7,11-methanocycloocta[b]quinolin-12-yl)amino]undecyl}-9,10-dihydro-4,5-dihydroxy-9,10-dioxoanthracene-2-carboxamide ($I_d$); and (±)-N-{4-{[(3-chloro-6,7,10,11-tetrahydro-9-methyl-7,11-methanocycloocta[b]quinolin-12-yl)amino]methyl}benzyl}-9,10-dihydro-4,5-dihydroxy-9,10-dioxoanthracene-2-carboxamide ($I_e$).

Compounds of formula (I) can be prepared by a process which comprises reacting a compound of formula (II), a salt or a reactive derivative thereof,

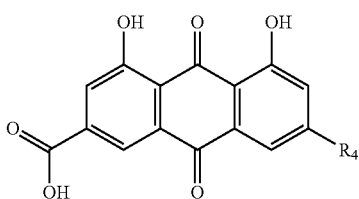

(II)

with a compound of formula (III) or a salt thereof, or any stereoisomer or mixture thereof, either of the compound of formula (III) or of their salts, where $R_4$ is H or OH,

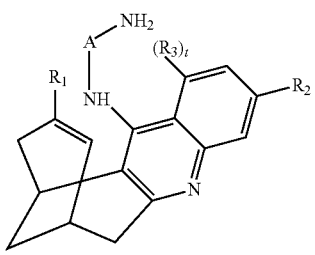

(III)

where $R_1$ is a ($C_1$-$C_2$) alkyl radical; $R_2$ and $R_3$ are radicals independently selected from the group consisting of F, Cl and methyl; A is a birradical selected from the group consisting of —($CH_2$)$_n$— and —($CH_2$)-phenyl-($CH_2$)—; t is an integer from 0 to 1; and n is an integer from 8 to 15; and, optionally, converting the compound thus obtained into a pharmaceutically acceptable salt by reacting it with a pharmaceutically acceptable acid.

Reactive derivatives of carboxylic acids include acyl halides, anhydrides, and esters. The carboxy group of compound (II) can be converted into an acyl halide, for example an acid chloride, for example by treating the compound (II) with a thionyl halide, for example thionyl chloride. The carboxyl group of the compound of formula (II) can also be converted into an anhydride, including a mixed anhydride, for example, using a formic acid ester such as a ($C_1$-$C_7$)alkyl ester. It can be carried out for example by treating a salt of compound (II), such as an ammonium or alkali metal salt, with a haloformic acid ester, such as a chloroformic acid ester, such as a ($C_1$-$C_7$)alkyl ester. The carboxy group of compound (II) can also be converted into an activated ester, such as a cyanomethyl ester, a nitrophenyl ester, for example a 4-nitrophenyl ester, or a polyhalophenyl ester, for example a pentachlorophenyl ester. It can be made by treating the compound of formula (II) with an appropriate hydroxyl compound in the presence of a suitable condensing agent, such as N,N'-dicyclohexylcarbodiimide.

As mentioned above the reactive derivative of this type can be reacted with an amine and in this way amide compounds of the formula (I) can be obtained. In this case, these can be obtained directly or via intermediate compounds such those describe above. Other non-activated esters, such as ($C_1$-$C_7$) alkyl esters of compounds of the formula (II), which contain, for example, ($C_2$-$C_8$)alkoxycarbonyl as a substituent, can also be brought to reaction with amines. Generally, the reaction is carried out in the presence of a base, preferably the base is selected from an alkaline or alkaline earth metal hydroxide or carbonate, for instance sodium or potassium hydroxide or sodium or potassium carbonate, and an organic amine, preferably a tertiary amine such as triethylamine.

The pharmaceutically acceptable salts of the compounds of formula (I), in particular, the hydrochlorides, but also other pharmaceutically acceptable salts of other acids such as hydrobromic, hydrofluoric, sulphuric, phosphoric, acetic, citric, fumaric, gluconic, lactic, maleic, succinic or tartaric acid, can be prepared conventionally, e.g. by mixing a solution of the free base and the acid in a suitable solvent, e.g. ethanol and recovering the acid addition salt either as precipitate, or by evaporation of the solution. Salts can also be converted into the free compounds in a customary manner, for example, by treating with a suitable basic agent.

In view of the close relationship between the novel compounds in the free base form and in the form of their salts, in the preceding text and below when it is referred to the compounds (I) may be understood as meaning either the free base compounds or their salts.

As mentioned above, the compounds of formula (I) or their salts can also be obtained in the form of their hydrates or can include other solvents used for crystallization. The obtention of solvates and hydrates depends on the solvent used and the crystallization conditions that can be determined by the skilled person. The new compounds herein described have the ability to retain molecules of water, which in some cases cannot be removed after drying the analytical samples at 65° C./2 Torr for 7 days.

Depending on the choice of the starting materials and processes, the compounds of formula (I) can be present in the form of one of the possible isomers or as mixtures thereof, for example as pure optical isomers, or as isomer mixtures, such as racemates, or stereoisomer mixtures.

Racemates and diastereomer mixtures obtained can be separated into the pure isomers or racemates in a known manner on the basis of the physicochemical differences of the components, for example by fractional crystallization. Racemates obtained may furthermore be resolved into the optical enantiomers by known methods, for example by recrystallization from an optically active solvent, chromatography on chiral adsorbents, with the aid of suitable microorganisms, by cleavage with specific immobilized enzymes, via the formation of inclusion compounds or by conversion into diastereomeric salts. Thus, for example a racemic compound of formula (I) can be separated into its enantiomers by reaction of the racemate with an optically active acid, such as a carboxylic acid, for example tartaric, malic acid, or a sulfonic acid, for example camphorsulfonic acid; and separation of the diastereomer mixture obtained in this manner, for example on the basis of its differing solubilities. Then, the desired enantiomer can be liberated by the action of suitable agents. The most active enantiomer is advantageously isolated. The separation of a racemic compound into its enantiomers can also be carried out over any of the intermediates that contain the huprine fragment, i.e. any of the intermediate compounds (III), (IV), or (V). Preferably, the separation is carried out over the compound of formula (V), for instance by chromatography on chiral adsorbents.

Compounds of formula (III) or their salts can be prepared by a process which comprises submitting a compound of formula (IV) or a salt thereof, or any stereoisomer or mixture thereof, either of the compound of formula (IV) or of their salts,

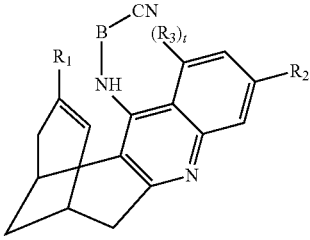

(IV)

where B is a birradical selected from the group consisting of —($CH_2$)$_{n-1}$— and —($CH_2$)-phenyl-; n is an integer from 8 to 15; and $R_1$, $R_2$, $R_3$, and t have the same meaning as for compound of formula (III), to a reduction reaction.

The reduction reaction can be carried out using a reducing agent, for instance lithium aluminum hydride in the presence of a suitable solvent, for instance, a ($C_2$-$C_6$) ether such as diethyl ether or tetrahydrofuran.

Compounds of formula (IV) where B is —$(CH_2)_{n-1}$— and n is an integer from 8 to 15, can be prepared by a process which comprises reacting a compound of formula (V) or a salt thereof, or any stereoisomer or mixture thereof, either of the compound of formula (V) or of their salts, with a compound of formula (VI). In compound of formula (V) $R_1$, $R_2$, $R_3$, and t have the same meaning as for compound of formula (III), and in compound of formula (VI) m is an integer from 7 to 14,

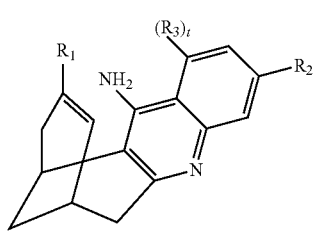
(V)

(VI)

Compounds of formula (IV) where B is —$(CH_2)$-phenyl-, i.e. compounds of formula ($IV_e$),

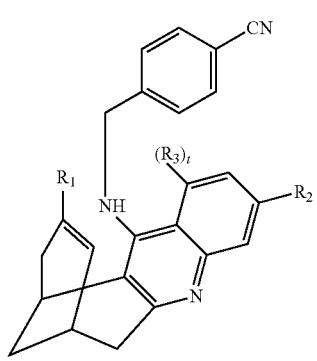
($IV_e$)

can be prepared by a process which comprises reacting a compound of formula (V) or a salt thereof, or any stereoisomer or mixture thereof, either of the compound of formula (V) or of their salts, with p-cyanobenzaldehyde to yield a compound of formula ($IV'_e$) where $R_1$, $R_2$, $R_3$, and t have the same meaning as for compound of formula (III). The reaction is generally carried out in the presence of a base, preferably an organic base, more preferably, the base is morfoline.

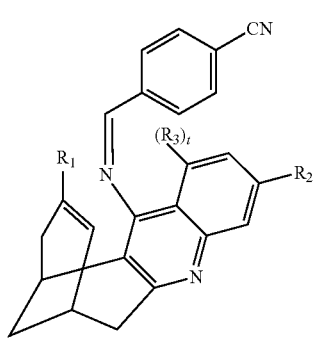
($IV'_e$)

The compound of formula ($IV'_e$) is then submitted to a reduction reaction to yield a compound of formula ($IV_e$). This reduction reaction can be carried out with a reducing agent, such as sodium cyanoborohydride in the presence of a suitable solvent, such as acetic acid.

The intermediate compounds of formula (III) or their salts, or any stereoisomer or mixture thereof, where $R_1$ is a ($C_1$-$C_2$) alkyl radical; $R_2$ and $R_3$ are radicals independently selected from the group consisting of F, Cl and methyl; A is a birradical selected from the group consisting of —$(CH_2)_n$— and —$(CH_2)$-phenyl-$(CH_2)$—; t is an integer from 0 to 1; and n is an integer from 8 to 15; are also part of the invention.

The intermediate compounds of formula (IV) or theirs salts, or any stereoisomer or mixture thereof, where B is a birradical selected from the group consisting of —$(CH_2)_{n-1}$— and —$(CH_2)$-phenyl-; n is an integer from 8 to 15; and $R_1$, $R_2$, $R_3$, and t have the same meaning as for compound of formula (III), are also part of the invention. The compound of formula ($IV'_e$) as defined above is also part of the invention.

The preferred values of $R_1$, $R_2$, $R_3$, and t mentioned for the compound of formula (I) are also preferred values for the compound of formula (III), (IV), ($IV_e$), ($IV'_e$), and (V).

Another aspect of the present invention relates to a pharmaceutical composition comprising a therapeutically effective amount of the compound of formula (I), or a pharmaceutically acceptable salt thereof, including any stereoisomer or mixture thereof, together with appropriate amounts of one or more pharmaceutical excipients or carriers.

The term "therapeutically effective amount" as used herein, refers to the amount of a compound that, when administered, is sufficient to prevent development of, or alleviate to some extent, one or more of the symptoms of AD. The particular dose of compound administered according to this invention will of course be determined by the particular circumstances surrounding the case, including the compound administered, the route of administration, the particular condition being treated, and the similar considerations.

The term "pharmaceutical composition" refers to a mixture of a compound disclosed herein with other chemical components, such as diluents or carriers. The pharmaceutical composition facilitates administration of the compound to an organism.

The terms "pharmaceutically acceptable excipients or carriers" refer to pharmaceutically acceptable material, composition or vehicle, such as liquid or solid filler, diluent, excipient, solvent, or encapsulating material. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

The term "treatment" meant to include alleviating or eradicating a disorder, disease, or condition, or one or more of the symptoms associated with the disorder, disease or condition, or alleviating or eradicating the cause(s) of the disorder, disease, or condition itself.

As it has been mentioned above and is illustrated in the Examples, the compounds of the present invention have the ability to inhibit in vitro BACE-1, AChE, BChE, and AChE-induced and self-induced β-amyloid Aβ aggregation, as well as to reduce in vivo Aβ42 and tau protein aggregation, synaptic failure, amyloid pathology and cognitive impairment.

Accordingly, another aspect of the invention relates to the compounds of formula (I) as defined above, for use as a medicament.

A further aspect of the present invention relates to the compounds of formula (I) as defined above for the prophylactic and/or therapeutic treatment of Alzheimer's disease in a mammal, including a human. This aspect can also be formulated as the use of the compounds of formula (I) as defined above, for the preparation of a medicament for the prophylactic and/or therapeutic treatment of Alzheimer's disease in a mammal, including a human. The invention also relates to a method of treatment and/or prophylaxis of a mammal, including a human, suffering from or being susceptible to AD, said method comprises the administration to said patient of a therapeutically effective amount of the compound of formula (I) as defined above, together with pharmaceutically acceptable excipients or carriers.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

FIG. 3 shows the results of electrophysiology studies in hippocampal slices of 2-month-old C57bl6 male mice incubated with Aβ oligomers and compounds of formula (−)-$(I_b)$ and (+)-$(I_b)$ (referred to as H9A(−) and H9A(+), respectively).

FIG. 4 shows the changes in synaptic protein levels of hippocampal slices of 2-month-old C57bl6 male mice treated with Aβ oligomers and compounds of formula (−)-$(I_b)$ and (+)-$(I_b)$.

FIG. 8 shows the amount of senile plaques present in 6- and 11-month-old APP-PS1 mice treated with compounds of formula (−)-$(I_b)$ and (+)-$(I_b)$, using Th-S staining.

FIG. 9 shows the effects of compounds of formula (−)-$(I_b)$ and (+)-$(I_b)$ on neuroinflammation in brain of 6- and 11-month-old APP-PS1 mice, using immunostaining with anti-GFAP.

EXAMPLES

Chemistry General Methods

Figure 1:
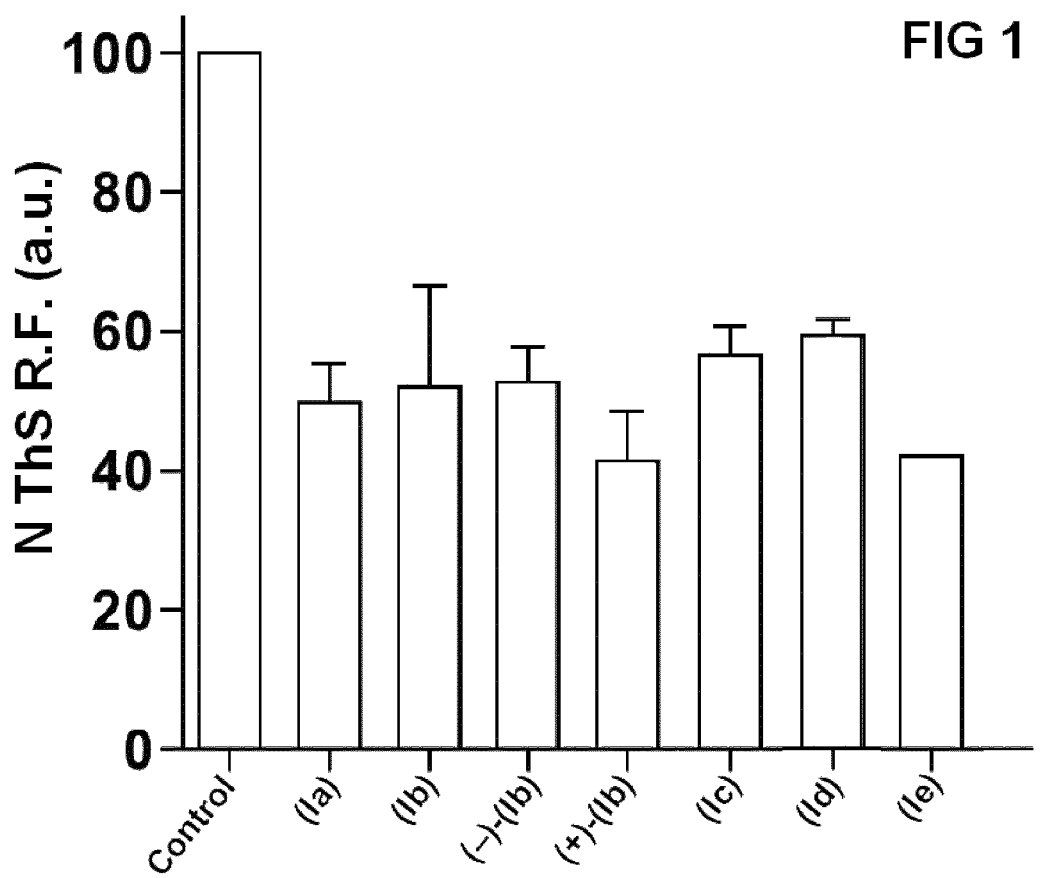
FIG. 1 shows the normalized thioflavin-S (Th-S) fluorescence in samples of *Escherichia coli* BL21 (DE3) overexpressing Aβ42 in the absence and in the presence of compounds of formula $(I_a)$-$(I_e)$, (−)-$(I_b)$ and (+)-$(I_b)$, as a measure of their effect on Aβ42 aggregation.

Melting points were determined in open capillary tubes with a MFB 595010M Gallenkamp melting point apparatus.

Elemental analyses and high resolution mass spectra were carried out at the Mycroanalysis Service of the IIQAB (CSIC, Barcelona, Spain) with a Carlo Erba model 1106 analyzer, and at the Centres Cientifics i Tecnòogics of the University of Barcelona with a LC/MSD TOF Agilent Technologics spectrometer.

IR spectra were run on a Perkin-Elmer Spectrum RX I spectrophotometer. Absorption values are expressed as wavenumbers ($cm^{-1}$); only significant absorption bands are given.

Column chromatography was performed on silica gel 60 AC.C (40-60 mesh, SDS, ref 2000027). Thin-layer chromatography was performed with aluminum-backed sheets with silica gel 60 F254 (Merck, ref 1.05554), and spots were visualized with UV light and 1% aqueous solution of $KMnO_4$.

Analytical grade solvents were used for crystallization, while pure for synthesis solvents were used in the reactions, extractions and column chromatography.

For characterization purposes, the new hybrids were transformed into the corresponding hydrochlorides, and recrystallized. The analytical samples of all of the new hybrids which were subjected to pharmacological evaluation possess a purity ≥95% as evidenced by their elemental analyses. Worthy of note, as previously reported for some tacrine-related dimeric compounds, the new hybrids herein described have the ability to retain molecules of water, which cannot be removed after drying the analytical samples at 65° C./2 Torr for 7 days. Thus, the elemental analyses of these compounds showed the presence of variable amounts of water, which have been indicated in the corresponding compound formulas.

Example 1

Preparation of (±)-8-[(3-chloro-6,7,10,11-tetrahydro-9-methyl-7,11-methanocycloocta[b]quinolin-12-yl) amino]octanenitrile ($IV_a$)

A well stirred suspension of (±)-huprine Y.HCl (V) (1.86 g, 5.80 mmol) and finely powdered NaOH (1.17 g, 29.2 mmol) in anhydrous DMSO (50 mL) was heated every 10 min approximately with a heat gun for 1 h and at room temperature for one additional hour, and then treated with a solution of 8-bromooctanenitrile ($VI_a$) (1.39 g, 6.81 mmol) in DMSO (30 mL). The reaction mixture was stirred at room temperature overnight, diluted with aqueous 5 N NaOH (150 mL) and extracted with AcOEt (3×120 mL). The combined organic extracts were washed with water (4×150 mL), dried with anhyd. $Na_2SO_4$, filtered and evaporated under reduced pressure to give a yellow oil (2.30 g), which was subjected to column chromatography [40-60 μm silica gel (100 g), $CH_2Cl_2$/50% aq $NH_4OH$ 100:0.2], to provide the compound of the title (1.00 g, 42% yield) as a yellowish solid. The isolated compound of the title was transformed into the corresponding hydrochloride as follows: A solution of the free base (41.0 mg, 0.10 mmol) in $CH_2Cl_2$ (3 mL) was filtered through a 0.2 μm PTFE filter and treated with a 0.43 N methanolic solution of HCl (0.7 mL, 0.30 mmol). The solution was concentrated in vacuo to dryness and the solid residue was washed with pentane (3×2 mL) and dried at 65° C./2 Torr for 7 days to give (±)-($IV_a$).HCl (41.6 mg) as a yellowish solid. Characterization: (±)-($IV_a$): $R_f$=0.65 ($CH_2Cl_2$/MeOH/ 50% aq $NH_4OH$ 9:1:0.05). (±)-($IV_a$).HCl: mp 129-130° C. ($CH_2Cl_2$/MeOH 81:19); IR (KBr) v: 3500-2500 (max at 3397, 3244, 3108, 3048, 3007, 2925, 2852, N—H, $^+$N—H, and C—H st), 2242 (CN st), 1701, 1624, 1562 (ar-C—C and ar-C—N st) cm$^{-1}$; HRMS (ESI) calcd for (C$_{25}$H$_{30}$$^{35}$ClN$_3$+H$^+$) 408.2201. found 408.2203.

Example 2

Preparation of (±)-9-[(3-chloro-6,7,10,11-tetrahydro-9-methyl-7,11-methanocycloocta[b]quinolin-12-yl)amino]nonanenitrile (IV$_b$)

It was prepared as described for the compound of Example 1. From (±)-huprine Y.HCl (V) (1.89 g, 5.90 mmol) and a solution of 9-bromononanenitrile (VI$_b$) (1.56 g, 7.19 mmol) in anhydrous DMSO (30 mL), a yellow oily residue (2.86 g) was obtained and subjected to column chromatography [40-60 μm silica gel (100 g), CH$_2$Cl$_2$/50% aq NH$_4$OH 100:0.2], to provide the compound of the title (1.65 g, 66% yield) as a yellowish solid. Characterization: (±)-(IV$_b$): R$_f$=0.56 (CH$_2$Cl$_2$/MeOH/50% aq NH$_4$OH 9:1:0.05). (±)-(IV$_b$).HCl: mp 121-123° C. (CH$_2$Cl$_2$/MeOH 82:18); IR (KBr) v: 3500-2500 (max at 3228, 3108, 3048, 3001, 2926, 2854, 2745, N—H, $^+$N—H, and C—H st), 2242 (CN st), 1718, 1630, 1582, 1569, 1501 (ar-C—C and ar-C—N st) cm$^{-1}$; HRMS (ESI) calcd for (C$_{26}$H$_{32}$$^{35}$ClN$_3$+H$^+$) 422.2358. found 422.2363.

Example 3

Preparation of (−)-(7S,11S)-9-[(3-chloro-6,7,10,11-tetrahydro-9-methyl-7,11-methanocycloocta[b]quinolin-12-yl)amino]nonanenitrile (−)-(IVb)

It was prepared as described for the compound of Example 1. From (−)-huprine Y (−)-(V) (>99% ee, 1.50 g, 5.28 mmol) and a solution of 9-bromononanenitrile (VI$_b$) (1.39 g, 6.40 mmol) in anhydrous DMSO (30 mL), a yellow oily residue (2.20 g) was obtained and subjected to column chromatography [40-60 μm silica gel (90 g), CH$_2$Cl$_2$/50% aq NH$_4$OH 100:0.2], to provide the compound of the title (750 mg, 34% yield) as a yellowish solid. Characterization: (−)-(IV$_b$): R$_f$=0.56 (CH$_2$Cl$_2$/MeOH/50% aq NH$_4$OH 9:1:0.05). (−)-(IV$_b$).HCl: mp 106-107° C. (CH$_2$Cl$_2$/MeOH 89:11); [α]$^{20}_D$=−212 (c=0.10, MeOH); IR (KBr) v: 3500-2500 (max at 3341, 3136, 3064, 2928, 2858, 2671, N—H, $^+$N—H, and C—H st), 2245 (CN st), 1605, 1573, 1525 (ar-C—C and ar-C—N st) cm$^{-1}$; HRMS (ESI) calcd for (C$_{26}$H$_{32}$$^{35}$ClN$_3$+H$^+$) 422.2358. found 422.2362.

Example 4

Preparation of (+)-(7R,11R)-9-[(3-chloro-6,7,10,11-tetrahydro-9-methyl-7,11-methanocycloocta[b]quinolin-12-yl)amino]nonanenitrile (+)-(IVb)

It was prepared as described for the compound of Example 1. From (+)-huprine Y (+)-(V) (>99% ee, 1.50 g, 5.28 mmol) and a solution of 9-bromononanenitrile (VI$_b$) (1.39 g, 6.40 mmol) in anhydrous DMSO (30 mL), a yellow oily residue (2.20 g) was obtained and subjected to column chromatography [40-60 μm silica gel (90 g), CH$_2$Cl$_2$/50% aq NH$_4$OH 100:0.2], to provide the compound of the title (929 mg, 42% yield) as a yellowish solid. Characterization: (+)-(IV$_b$): R$_f$=0.56 (CH$_2$Cl$_2$/MeOH/50% aq NH$_4$OH 9:1:0.05). (+)-(IV$_b$).HCl: mp 109-111° C. (CH$_2$Cl$_2$/MeOH 93:7); [α]$^{20}_D$=+213 (c=0.10, MeOH); IR (KBr) v: 3500-2500 (max at 3379, 3228, 3111, 3038, 3007, 2926, 2854, N—H, $^+$N—H, and C—H st), 2242 (CN st), 1627, 1620, 1576, 1558, 1542, 1522, 1511 (ar-C—C and ar-C—N st) cm$^{-1}$; HRMS (ESI) calcd for (C$_{26}$H$_{32}$$^{35}$ClN$_3$+H$^+$) 422.2358. found 422.2356.

Example 5

Preparation of (±)-10-[(3-chloro-6,7,10,11-tetrahydro-9-methyl-7,11-methanocycloocta[b]quinolin-12-yl)amino]decanenitrile (IV$_c$)

It was prepared as described for the compound of Example 1. From (±)-huprine Y (V) (2.00 g, 7.02 mmol) and a solution of 10-bromodecanenitrile (VI$_c$) (87% purity, 2.15 g, 8.07 mmol) in anhydrous DMSO (30 mL), a yellow oily residue (2.84 g) was obtained and subjected to column chromatography [40-60 μm silica gel (120 g), CH$_2$Cl$_2$/50% aq NH$_4$OH 100:0.2], to provide the compound of the title (756 mg, 25% yield) as a yellowish solid. Characterization: (±)-(IV$_c$): R$_f$=0.66 (CH$_2$Cl$_2$/MeOH/50% aq NH$_4$OH 9:1:0.05). (±)-(IV$_c$).HCl: mp 129-131° C. (CH$_2$Cl$_2$/MeOH 90:10); IR (KBr) v: 3500-2500 (max at 3229, 3105, 3047, 3007, 2926, 2853, 2740, 2640, N—H, $^+$N—H, and C—H st), 2242 (CN st), 1630, 1582, 1511 (ar-C—C and ar-C—N st) cm$^{-1}$; HRMS (ESI) calcd for (C$_{27}$H$_{34}$$^{35}$ClN$_3$+H$^+$) 436.2514. found 436.2508.

Example 6

Preparation of (±)-11-[(3-chloro-6,7,10,11-tetrahydro-9-methyl-7,11-methanocycloocta[b]quinolin-12-yl)amino]undecanenitrile (IV$_d$)

It was prepared as described for the compound of Example 1. From (±)-huprine Y (V) (1.70 g, 5.97 mmol) and a solution of 11-bromoundecanenitrile (VI$_d$) (80% purity, 2.11 g, 6.86 mmol) in anhydrous DMSO (10 mL), a yellow oily residue (2.20 g) was obtained and subjected to column chromatography [40-60 μm silica gel (90 g), CH$_2$Cl$_2$/50% aq NH$_4$OH 100:0.2], to provide the compound of the title (1.09 g, 41% yield) as a yellowish solid. Characterization: (±)-(IV$_d$): R$_f$=0.62 (CH$_2$Cl$_2$/MeOH/50% aq NH$_4$OH 9:1:0.05). (±)-(IV$_d$).HCl: mp 131-133° C. (CH$_2$Cl$_2$/MeOH 93:7); IR (KBr) v: 3500-2500 (max at 3853, 3744, 3395, 3231, 3111, 3048, 3012, 2925, 2853, 2742, 2645, N—H, $^+$N—H, and C—H st), 2242 (CN st), 1628, 1582, 1559, 1542, 1521, 1507 (ar-C—C and ar-C—N st) cm$^{-1}$; HRMS (ESI) calcd for (C$_{28}$H$_{36}$$^{35}$ClN$_3$+H$^+$) 450.2671. found 450.2664.

Example 7

Preparation of (±)-4-{[(3-chloro-6,7,10,11-tetrahydro-9-methyl-7,11-methanocycloocta[b]quinolin-12-yl)imino]methyl}benzonitrile (IV'$_e$)

To a suspension of (±)-huprine Y (V) (2.00 g, 7.02 mmol) in anhyd. toluene (19 mL), freshly distilled morpholine (0.67 mL, 0.67 g, 7.66 mmol) and p-cyanobenzaldehyde (1.80 g, 13.7 mmol) were added. The reaction mixture was stirred under reflux for 48 h and concentrated under reduced pressure. The resulting residue was subjected to column chromatography [40-60 μm silica gel (120 g), CH$_2$Cl$_2$], to provide the compound of the title (2.20 g, 79% yield) as a yellowish solid. Characterization: (±)-(IV'$_e$): R$_f$=0.17 (CH$_2$Cl$_2$); mp 208-210° C. (CH$_2$Cl$_2$); IR (KBr) v: 2225 (CN st), 1721, 1639, 1600, 1570, 1553, 1500 (ar-C—C and ar-C—N st) cm$^{-1}$; HRMS (ESI) calcd for (C$_{25}$H$_{20}$$^{35}$ClN$_3$+H$^+$) 398.1419. found 398.1426.

Example 8

Preparation of (±)-4-{[(3-chloro-6,7,10,11-tetrahydro-9-methyl-7,11-methanocyclooca[b]quinolin-12-yl)amino]methyl}benzonitrile ($IV_e$)

A solution of imine (±)-($IV'_e$) (2.30 g, 5.79 mmol) in glacial AcOH (40 mL) was treated with solid $NaBH_3CN$ (763 mg, 12.1 mmol) portionwise for 1 h. The resulting suspension was stirred at room temperature for 3 h, cooled to 0° C. with an ice bath, treated with aq 10 N NaOH, and extracted with AcOEt (2×200 mL). The combined organic extracts were dried with anhyd. $Na_2SO_4$, filtered, and concentrated under reduced pressure to give the compound of the title (2.10 g, 91% yield) as a yellow solid. This compound was transformed into the corresponding hydrochloride as follows: A solution of the free base (60 mg, 0.15 mmol) in $CH_2Cl_2$ (5 mL) was filtered through a 0.2 μm PTFE filter and treated with a 0.53 N methanolic solution of HCl (0.85 mL, 0.45 mmol). The solution was concentrated in vacuo to dryness and the solid residue was washed with pentane (3×2 mL) and dried at 65° C./2 Torr for 7 days to give (±)-($IV_e$).HCl (62 mg) as a yellow solid. Characterization: (±)-($IV_e$): $R_f$=0.75 ($CH_2Cl_2$/MeOH/50% aq $NH_4OH$ 9:1:0.05). (±)-($IV_e$).HCl: mp 217-218° C. ($CH_2Cl_2$); IR (KBr) v: 3500-2500 (max at 3229, 3101, 3050, 2999, 2901, 2722, N—H, $^+$N—H, and C—H st), 2226 (CN st), 1718, 1631, 1582, 1555, 1507 (ar-C—C and ar-C—N st) $cm^{-1}$; HRMS (ESI) calcd for ($C_{25}H_{22}{}^{35}ClN_3$+$H^+$) 400.1575. found 400.1582.

Example 9

Preparation of (±)-8-[(3-chloro-6,7,10,11-tetrahydro-9-methyl-7,11-methanocyclooca[b]quinolin-12-yl)amino]octan-1-amine ($III_a$)

A suspension of nitrile (±)-($IV_a$) (0.96 g, 2.36 mmol) in anhyd. $Et_2O$ (40 mL) was cooled to 0° C. with an ice bath and treated dropwise with a 4 M solution of $LiAlH_4$ in $Et_2O$ (1.77 mL 7.08 mmol). The reaction mixture was warmed to room temperature, stirred overnight, cooled to 0° C. and treated dropwise with a 4 M solution of $LiAlH_4$ in $Et_2O$ (0.80 mL 3.20 mmol). The resulting mixture was warmed to room temperature, stirred for an additional 3 h, cooled to 0° C., treated dropwise with aq 1 N NaOH (50 mL) and water (120 mL), and extracted with AcOEt (3×120 mL). The combined organic extracts were dried with anhyd. $Na_2SO_4$, filtered, and evaporated under reduced pressure to give the compound of the title (1.14 g, quantitative yield) as a yellowish oil. The compound of the title was transformed into the corresponding dihydrochloride as follows: A solution of the free base (73.0 mg, 0.18 mmol) in $CH_2Cl_2$ (10 mL) was filtered through a 0.2 μm PTFE filter and treated with a 0.53 N methanolic solution of HCl (3.0 mL, 1.59 mmol). The solution was concentrated in vacuo to dryness and the solid residue was washed with pentane (3×2 mL) and dried at 65° C./2 Torr for 7 days to give (±)-($III_a$).2HCl (53.0 mg) as a yellowish solid. Characterization: (±)-($III_a$): $R_f$=0.07 ($CH_2Cl_2$/MeOH/50% aq $NH_4OH$ 9:1:0.05). (±)-($III_a$).2HCl: mp 209-211° C. ($CH_2Cl_2$); IR (KBr) v: 3500-2500 (max at 3395, 3245, 2927, 2854, 2780, N—H, $^+$N—H, and C—H st), 1628, 1583, 1524, 1508, 1501 (ar-C—C and ar-C—N st) $cm^{-1}$; HRMS (ESI) calcd for ($C_{25}H_{34}{}^{35}ClN_3$+$H^+$) 412.2514. found 412.2509.

Example 10

Preparation of (±)-9-[(3-chloro-6,7,10,11-tetrahydro-9-methyl-7,11-methanocyclooca[b]quinolin-12-yl)amino]nonan-1-amine ($III_b$)

It was prepared as described for the compound of Example 9. From nitrile (±)-($IV_b$) (1.60 g, 3.79 mmol), the compound of the title (1.39 g, 87% yield) was obtained as a yellowish oil. Characterization: (±)-($III_b$): $R_f$=0.10 ($CH_2Cl_2$/MeOH/50% aq $NH_4OH$ 9:1:0.05). (±)-($III_b$).2HCl: mp 169-171° C. ($CH_2Cl_2$/MeOH 82:18); IR (KBr) v: 3500-2500 (max at 3397, 3245, 2925, 2853, 2795, N—H, $^+$N—H, and C—H st), 1629, 1582, 1508 (ar-C—C and ar-C—N st) $cm^{-1}$; HRMS (ESI) calcd for ($C_{26}H_{36}{}^{35}ClN_3$+$H^+$) 426.2671. found 426.2664.

Example 11

Preparation of (−)-(7S,11S)-9-[(3-chloro-6,7,10,11-tetrahydro-9-methyl-7,11-methanocyclooca[b]quinolin-12-yl)amino]nonan-1-amine (−)-($III_b$)

It was prepared as described for the compound of Example 9. From nitrile (−)-($IV_b$) (664 mg, 1.58 mmol), the compound of the title (652 mg, 97% yield) was obtained as a yellowish oil. Characterization: (−)-($III_b$): $R_f$=0.10 ($CH_2Cl_2$/MeOH/50% aq $NH_4OH$ 9:1:0.05). (−)-($III_b$).2HCl: mp 126-128° C. ($CH_2Cl_2$/MeOH 81:19); $[\alpha]^{20}_D$=170 (c=0.10, MeOH); IR (KBr) v: 3500-2500 (max at 3251, 2923, 2853, N H, $^+$N—H, and C—H st), 1629, 1582, 1512, 1501 (ar-C—C and ar-C—N st) $cm^{-1}$; HRMS (ESI) calcd for ($C_{26}H_{36}{}^{35}ClN_3$+$H^+$) 426.2671. found 426.2656.

Example 12

Preparation of (+)-(7R,11R)-9-[(3-chloro-6,7,10,11-tetrahydro-9-methyl-7,11-methanocyclooca[b]quinolin-12-yl)amino]nonan-1-amine (+)-($III_b$)

It was prepared as described for the compound of Example 9. From nitrile (+)-($IV_b$) (499 mg, 1.18 mmol), the compound of the title (429 mg, 86% yield) was obtained as a yellowish oil. Characterization: (+)-($III_b$): $R_f$=0.10 ($CH_2Cl_2$/MeOH/50% aq $NH_4OH$ 9:1:0.05). (+)-($III_b$).2HCl: mp 127-128° C. ($CH_2Cl_2$/MeOH 65:35); $[\alpha]^{20}_D$=+186 (c=0.10, MeOH); IR (KBr) v: 3500-2500 (max at 3250, 2922, 2853, N—H, $^+$N—H, and C—H st), 1629, 1582, 1512 (ar-C—C and ar-C—N st) $cm^{-1}$; HRMS (ESI) calcd for ($C_{26}H_{36}{}^{35}ClN_3$+$H^+$) 426.2671. found 426.2668.

Example 13

Preparation of (±)-10-[(3-chloro-6,7,10,11-tetrahydro-9-methyl-7,11-methanocyclooca[b]quinolin-12-yl)amino]decan-1-amine ($III_c$)

It was prepared as described for the compound of Example 9. From nitrile (±)-($IV_c$) (645 mg, 1.47 mmol), the compound of the title (581 mg, 90% yield) was obtained as a yellowish oil. Characterization: (±)-($III_c$): $R_f$=0.06 ($CH_2Cl_2$/MeOH/50% aq $NH_4OH$ 9:1:0.05). (±)-($III_c$).2HCl: mp 179-180° C. ($CH_2Cl_2$/MeOH 89:11); IR (KBr) v: 3500-2500 (max at 3382, 3235, 2997, 2926, 2853, 2790, N—H, $^+$N—H, and C—H st), 1630, 1582, 1512 (ar-C—C and ar-C—N st) $cm^{-1}$; HRMS (ESI) calcd for ($C_{27}H_{38}{}^{35}ClN_3$+$H^+$) 440.2827. found 440.2820.

Example 14

Preparation of (±)-11-[(3-chloro-6,7,10,11-tetrahydro-9-methyl-7,11-methanocycloocta[b]quinolin-12-yl)amino]undecan-1-amine (III$_d$)

It was prepared as described for the compound of Example 9. From nitrile (±)-(IV$_d$) (1.05 g, 2.34 mmol), the compound of the title (848 mg, 80% yield) was obtained as a yellowish oil. Characterization: (±)-(IV$_d$): R$_f$=0.05 (CH$_2$Cl$_2$/MeOH/ 50% aq NH$_4$OH 9:1:0.05). (±)-(IV$_d$).2HCl: mp 164-165° C. (CH$_2$Cl$_2$/MeOH 79:21); IR (KBr) ν: 3500-2500 (max at 3385, 3232, 3043, 2924, 2852, 2790, 2651, N—H, $^+$N—H, and C—H st), 1630, 1582, 1512 (ar-C—C and ar-C—N st) cm$^{-1}$; HRMS (ESI) calcd for (C$_{28}$H$_{40}$$^{35}$ClN$_3$+H$^+$) 454.2984. found 454.2969.

Example 15

Preparation of (±)-4-{[(3-chloro-6,7,10,11-tetrahydro-9-methyl-7,11-methanocycloocta[b]quinolin-12-yl)amino]methyl}benzylamine (III$_e$)

It was prepared as described for the compound of Example 9. From nitrile (±)-(IV$_e$) (370 mg, 0.93 mmol), the compound of the title (352 mg, 93% yield) was obtained as a yellowish oil. Characterization: (±)-(III$_e$): R$_f$=0.11 (CH$_2$Cl$_2$/MeOH/ 50% aq NH$_4$OH 9:1:0.05). (±)-(III$_e$).2HCl: mp 151-152° C. (CH$_2$Cl$_2$/MeOH 82:18); IR (KBr) ν: 3500-2500 (max at 3390, 3245, 3043, 3002, 2899, 2795, 2609, N—H, $^+$N—H, and C—H st), 1715, 1700, 1631, 1583, 1517 (ar-C—C and ar-C—N st) cm$^{-1}$; HRMS (ESI) calcd for (C$_{25}$H$_{26}$$^{35}$ClN$_3$+H$^+$) 403.1577. found 403.1577.

Example 16

Preparation of (±)-N-{8-[(3-chloro-6,7,10,11-tetrahydro-9-methyl-7,11-methanocycloocta[b]quinolin-12-yl)amino]octyl}-9,10-dihydro-4,5-dihydroxy-9,10-dioxoanthracene-2-carboxamide (I$_a$)

A suspension of 9,10-dihydro-4,5-dihydroxy-9,10-dioxoanthracene-2-carboxylic acid (II) (212 mg, 0.75 mmol) in anhyd. CH$_2$Cl$_2$ (7 mL) was cooled to 0° C. with an ice bath, and treated dropwise with anhyd. Et$_3$N (0.21 mL, 152 mg, 1.50 mmol) and ethyl chloroformate (0.72 mL, 82.4 mg, 0.75 mmol). The resulting mixture was stirred at 0° C. for 30 min and treated with a solution of amine (±)-(III$_a$) (307 mg, 0.75 mmol) in anhyd. CH$_2$Cl$_2$ (6 mL). The reaction mixture was stirred at room temperature for 3 days and treated with 10% aq Na$_2$CO$_3$ (50 mL). The phases were separated and the aqueous phase was further extracted with CH$_2$Cl$_2$ (3×100 mL). The combined organic extracts were dried with anhyd. Na$_2$SO$_4$, filtered, and evaporated under reduced pressure to give a red solid residue (740 mg), which was subjected to column chromatography [40-60 μm silica gel (44 g), hexane/ AcOEt/Et$_3$N mixtures]. On elution with hexane/AcOEt/Et$_3$N 98:2:0.2 to 80:20:0.2, impure compound of the title was isolated (165 mg), and subjected to a subsequent purification by column chromatography [40-60 μm silica gel (13 g), CH$_2$Cl$_2$/ MeOH/50% aq NH$_4$OH mixtures]. On elution with CH$_2$Cl$_2$/ MeOH/50% aq NH$_4$OH 98:2:0.2 to 90:10:0.2, the compound of the title (79.4 mg, 17% yield) was isolated as a red solid. The isolated compound of the title was transformed into the corresponding hydrochloride as follows: A solution of the free base (39.0 mg, 0.06 mmol) in CH$_2$Cl$_2$ (4 mL) was filtered through a 0.2 μm PTFE filter and treated with a 0.53 N methanolic solution of HCl (2.3 mL, 1.22 mmol). The solution was concentrated in vacuo to dryness and the solid residue was taken in CH$_2$Cl$_2$/MeOH 1:1 (0.4 mL) and precipitated with AcOEt (0.8 mL). The separated solid was washed with pentane (3×2 mL) and dried at 65° C./2 Torr for 7 days to give (±)-(I$_a$).HCl (32 mg) as a yellowish solid. Characterization: (±)-(I$_a$): R$_f$=0.30 (CH$_2$Cl$_2$/MeOH/50% aq NH$_4$OH 9:1: 0.05). (±)-(I$_a$).HCl: mp 180-182° C. (CH$_2$Cl$_2$/MeOH 82:18); IR (KBr) ν: 3500-2500 (max at 3222, 3047, 3007, 2924, 2852, 2640, O—H, N—H, $^+$N—H, and C—H st), 1674, 1628, 1607, 1582, 1566, 1522 (C=O, ar-C—C and ar-C—N st) cm$^{-1}$; HRMS (ESI) calcd for (C$_{40}$H$_{40}$$^{35}$ClN$_3$O$_5$+H$^+$) 678.2729. found 678.2734. Elemental analysis, calcd for (C$_{40}$H$_{40}$ClN$_3$O$_5$.HCl.H$_2$O) C, 65.57; H, 5.92; N, 5.73; Cl, 9.68. found C, 65.52; H, 5.86; N, 5.83; Cl, 9.35.

Example 17

Preparation of (±)-N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide (I$_b$)

It was prepared as described for the compound of Example 16. From 9,10-dihydro-4,5-dihydroxy-9,10-dioxoanthracene-2-carboxylic acid (II) (212 mg, 0.75 mmol) and amine (±)-(III$_b$) (321 mg, 0.75 mmol), a red solid residue (550 mg) was obtained and subjected to column chromatography [40-60 μm silica gel (33 g), hexane/AcOEt/Et$_3$N mixtures]. On elution with hexane/AcOEt/Et$_3$N 20:80:0.2 to 80:20:0.2, the compound of the title (118 mg, 23% yield) was isolated as a red solid. Characterization: (±)-(I$_b$): R$_f$=0.33 (CH$_2$Cl$_2$/ MeOH/50% aq NH$_4$OH 9:1:0.05). (±)-(I$_b$).HCl: mp 192-193° C. (CH$_2$Cl$_2$/MeOH 82:18); IR (KBr) ν: 3500-2500 (max at 3401, 2925, 2853, O—H, N—H, $^+$N—H, and C—H st), 1628, 1584, 1566, 1524 (C=O, ar-C—C and ar-C—N st) cm$^{-1}$; HRMS (ESI) calcd for (C$_{41}$H$_{42}$$^{35}$ClN$_3$O$_5$+H$^+$) 692.2886. found 692.2873. Elemental analysis, calcd for (C$_{41}$H$_{42}$ClN$_3$O$_5$.1.6HCl) C, 65.61; H, 5.85; N, 5.60; Cl, 12.28. found C, 65.23; H, 6.00; N, 5.50; Cl, 12.28.

Example 18

Preparation of (−)-(7S,11S)—N-{9-[(3-chloro-6,7, 10,11-tetrahydro-9-methyl-7,11-methanocycloocta [b]quinolin-12-yl)amino]nonyl}-9,10-dihydro-4,5-dihydroxy-9,10-dioxoanthracene-2-carboxamide (−)-(I$_b$)

It was prepared as described for the compound of Example 16. From 9,10-dihydro-4,5-dihydroxy-9,10-dioxoanthracene-2-carboxylic acid (II) (422 mg, 1.49 mmol) and amine (−)-(III$_b$) (632 mg, 1.49 mmol), a red solid residue (1.10 g) was obtained and subjected to column chromatography [40-60 μm silica gel (50 g), CH$_2$Cl$_2$/MeOH/50% aq. NH$_4$OH mixtures]. On elution with CH$_2$Cl$_2$/MeOH/50% aq. NH$_4$OH 99:1:0.2, the compound of the title (101 mg, 10% yield) was isolated as a red solid. Characterization: (−)-(I$_b$): R$_f$=0.33 (CH$_2$Cl$_2$/MeOH/50% aq NH$_4$OH 9:1:0.05). (−)-(I$_b$) .HCl: mp 168-170° C. (CH$_2$Cl$_2$/MeOH 83:17); [α]$^{20}$$_D$=−154 (c=0.10, MeOH); IR (KBr) ν: 3500-2500 (max at 3226, 3048, 3002, 2925, 2853, 2743, O—H, N—H, $^+$N—H, and C—H st), 1766, 1705, 1675, 1629, 1604, 1582, 1566, 1524, 1509 (C=O, ar-C—C and ar-C—N st) cm$^{-1}$; HRMS (ESI) calcd for (C$_{41}$H$_{42}$$^{35}$ClN$_3$O$_5$+H$^+$) 692.2886. found 692.2891.

Elemental analysis, calcd for ($C_{41}H_{42}ClN_3O_5 \cdot HCl \cdot H_2O$) C, 65.95; H, 6.07; N, 5.63; Cl, 9.50. found C, 65.50; H, 6.07; N, 5.20; Cl, 9.91.

Example 19

Preparation of (+)-(7R,11R)—N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide (±)-($I_b$)

It was prepared as described for the compound of Example 16. From 9,10-dihydro-4,5-dihydroxy-9,10-dioxoanthracene-2-carboxylic acid (II) (477 mg, 1.68 mmol) and amine (+)-(III$_b$) (715 mg, 1.68 mmol), a red solid residue (1.50 g) was obtained and subjected to column chromatography [40-60 µm silica gel (50 g), $CH_2Cl_2$/MeOH/50% aq. $NH_4OH$ mixtures]. On elution with $CH_2Cl_2$/MeOH/50% aq. $NH_4OH$ 99:1:0.2, the compound of the title (191 mg, 16% yield) was isolated as a red solid. Characterization: (+)-($I_b$): $R_f$=0.33 ($CH_2Cl_2$/MeOH/50% aq $NH_4OH$ 9:1:0.05). (+)-($I_b$) .HCl: mp 164-165° C. ($CH_2Cl_2$/MeOH 88:12); $[α]^{20}_D$=+154 (c=0.10, MeOH); IR (KBr) v: 3500-2500 (max at 3226, 3049, 2926, 2852, O—H, N—H, $^+$N—H, and C—H st), 1763, 1739, 1723, 1710, 1656, 1629, 1583, 1566, 1555, 1537, 1511, 1501 (C=O, ar-C—C and ar-C—N st) cm$^{-1}$; HRMS (ESI) calcd for ($C_{41}H_{42}{}^{35}ClN_3O_5$+H$^+$) 692.2886. found 692.2877. Elemental analysis, calcd for ($C_{41}H_{42}ClN_3O_5 \cdot 1.25HCl \cdot 0.75H_2O$) C, 65.54; H, 6.00; N, 5.59; Cl, 10.62. found C, 65.79; H, 6.28; N, 5.80; Cl, 10.89.

Example 20

Preparation of (±)-N-{10-[(3-chloro-6,7,10,11-tetrahydro-9-methyl-7,11-methanocycloocta[b]quinolin-12-yl)amino]decyl}-9,10-dihydro-4,5-dihydroxy-9,10-dioxoanthracene-2-carboxamide ($I_c$)

It was prepared as described for the compound of Example 16. From 9,10-dihydro-4,5-dihydroxy-9,10-dioxoanthracene-2-carboxylic acid (II) (341 mg, 1.20 mmol) and amine (±)-(III$_c$) (530 mg, 1.20 mmol), a red solid residue (900 mg) was obtained and subjected to column chromatography [40-60 µm silica gel (50 g), $CH_2Cl_2$/MeOH/50% aq $NH_4OH$ mixtures]. On elution with $CH_2Cl_2$/MeOH/50% aq $NH_4OH$ 99:1:0.2, the compound of the title (115 mg, 14% yield) was isolated as a red solid. Characterization: (±)-($I_c$): $R_f$=0.53 ($CH_2Cl_2$/MeOH/50% aq $NH_4OH$ 9:1:0.05). (±)-($I_c$).HCl: mp 171-173° C. (AcOEt/$CH_2Cl_2$/MeOH 72:14:14); IR (KBr) v: 3500-2500 (max at 3229, 3049, 3002, 2925, 2852, O—H, N—H, $^+$N—H, and C—H st), 1767, 1739, 1715, 1675, 1629, 1604, 1583, 1567, 1524 (C=O, ar-C—C and ar-C—N st) cm$^{-1}$; HRMS (ESI) calcd for ($C_{42}H_{44}{}^{35}ClN_3O_5$+H$^+$) 706.3042. found 706.3038. Elemental analysis, calcd for ($C_{42}H_{44}ClN_3O_5 \cdot HCl \cdot 0.5H_2O$) C, 67.11; H, 6.17; N, 5.59; Cl, 9.43. found C, 66.88; H, 6.31; N, 5.29; Cl, 9.91.

Example 21

Preparation of (±)-N-{11-[(3-chloro-6,7,10,11-tetrahydro-9-methyl-7,11-methanocycloocta[b]quinolin-12-yl)amino]undecyl}-9,10-dihydro-4,5-dihydroxy-9,10-dioxoanthracene-2-carboxamide ($I_d$)

It was prepared as described for the compound of Example 16. From 9,10-dihydro-4,5-dihydroxy-9,10-dioxoanthracene-2-carboxylic acid (II) (491 mg, 1.73 mmol) and amine (±)-(III$_d$) (785 mg, 1.73 mmol), a red solid residue (1.60 g) was obtained and subjected to column chromatography [40-60 µm silica gel (50 g), $CH_2Cl_2$/MeOH/50% aq $NH_4OH$ mixtures]. On elution with $CH_2Cl_2$/MeOH/50% aq $NH_4OH$ 99:1:0.2, the compound of the title (338 mg, 27% yield) was isolated as a red solid. Characterization: (±)-($I_d$): $R_f$=0.50 ($CH_2Cl_2$/MeOH/50% aq $NH_4OH$ 9:1:0.05). (±)-($I_d$) .HCl: mp 171-172° C. (AcOEt/$CH_2Cl_2$/MeOH 1:1:3); IR (KBr) v: 3500-2500 (max at 3226, 3048, 3007, 2924, 2852, 2645, O—H, N—H, $^+$N—H, and C—H st), 1765, 1675, 1628, 1607, 1583, 1567, 1522 (C=O, ar-C—C and ar-C—N st) cm$^{-1}$; HRMS (ESI) calcd for ($C_{43}H_{46}{}^{35}ClN_3O_5$+H$^+$) 720.3199. found 720.3195. Elemental analysis, calcd for ($C_{43}H_{46}{}^{35}ClN_3O_5 \cdot HCl \cdot 0.5H_2O$) C, 67.44; H, 6.32; N, 5.49; Cl, 9.26. found C, 67.52; H, 6.46; N, 5.30; Cl, 9.51.

Example 22

Preparation of (±)-N-{4-{[(3-chloro-6,7,10,11-tetrahydro-9-methyl-7,11-methanocycloocta[b]quinolin-12-yl)amino]methyl}benzyl}-9,10-dihydro-4,5-dihydroxy-9,10-dioxoanthracene-2-carboxamide ($I_e$)

It was prepared as described for the compound of Example 16. From 9,10-dihydro-4,5-dihydroxy-9,10-dioxoanthracene-2-carboxylic acid (II) (548 mg, 1.93 mmol) and amine (±)-(III$_e$) (780 mg, 1.93 mmol), a red solid residue (1.07 g) was obtained and subjected to column chromatography [40-60 µm silica gel (40 g), hexane/AcOEt/Et$_3$N mixtures]. On elution with hexane/AcOEt/Et$_3$N 40:60:0.2, the compound of the title (113 mg, 9% yield) was isolated as a red solid. Characterization: (±)-($I_e$): $R_f$=0.57 ($CH_2Cl_2$/MeOH/50% aq $NH_4OH$ 9:1:0.05). (±)-($I_e$).HCl: mp 129-130° C. ($CH_2Cl_2$/MeOH 82:18); IR (KBr) v: 3500-2500 (max at 3245, 3055, 2925, 2852, 2790, O—H, N—H, $^+$N—H, and C—H st), 1705, 1673, 1629, 1607, 1583, 1560, 1516 (C=O, ar-C—C and ar-C—N st) cm$^{-1}$; HRMS (ESI) calcd for ($C_{40}H_{32}{}^{35}ClN_3O_5$+H$^+$) 670.2103. found 670.2104. Elemental analysis, calcd for ($C_{40}H_{32}{}^{35}ClN_3O_5 \cdot 1.1HCl \cdot 1.4H_2O$) C, 65.32; H, 4.92; N, 5.71; Cl, 10.12. found C, 65.32; H, 5.05; N, 6.17; Cl, 10.15.

Example 23

β-Secretase (BACE-1) Inhibition Assay

β-Secretase (BACE-1, Sigma) inhibition studies were performed by employing a peptide mimicking APP sequence as substrate (methoxycoumarin-Ser-Glu-Val-Asn-Leu-Asp-Ala-Glu-Phe-Lys-dinitrophenyl, M-2420, Bachem). The following procedure was employed: 5 µL of test compound (or DMSO, if preparing a control well) were pre-incubated with 175 µL of the enzyme (in 20 mM sodium acetate containing CHAPS 0.1% w/v) for 1 h at room temperature. The substrate (3 µM, final concentration) was then added and left to react for 15 min. The fluorescence signal was read at $λ_{em}$=405 nm ($λ_{exc}$=320 nm). The DMSO concentration in the final mixture maintained below 5% (v/v) guaranteed no significant loss of enzyme activity. The fluorescence intensities with and without inhibitor were compared and the percent inhibition due to the presence of test compounds was calculated. The background signal was measured in control wells containing all the reagents, except BACE-1 and subtracted. The % inhibition due to the presence of increasing test compound concentration was calculated by the following expression: 100−(IF$_i$/IF$_o$×100) where IF$_i$ and IF$_o$ are the fluorescence intensities obtained for BACE-1 in the presence and in the absence of inhibitor, respectively. Inhibition curves were obtained by plotting the % inhibition versus the logarithm of inhibitor concentration in the assay sample. The linear regression parameters were determined and the $IC_{50}$ extrapolated (GraphPad Prism 4.0, GraphPad Software Inc.). To demonstrate inhibition of BACE-1 activity a peptido-mimetic inhibitor (β-secretase inhibitor IV, Calbiochem) was serially diluted into the reactions' wells ($IC_{50}$=13±0.1 nM).

The results of BACE-1 inhibitory activities of the hydrochlorides of racemic and enantiopure huprine Y, and the hydrochlorides of racemic compounds of formula $(I_a)$-$(I_e)$ and enantiopure compounds $(-)$-$(I_b)$ and $(+)$-$(I_b)$ are summarized in Table 1 below.

All of the compounds of formula $(I_a)$-$(I_e)$ and $(-)$-$(I_b)$ and $(+)$-$(I_b)$ exhibit a significant BACE-1 inhibition, exhibiting $IC_{50}$ values in the nanomolar to low micromolar range, they being clearly more potent than the parent huprine Y. The most potent compounds, $(-)$-$(I_b)$ and $(+)$-$(I_b)$ ($IC_{50}$=80 nM), are 3-fold more potent than the promising Eli Lilly BACE-1 inhibitor LY2811376 ($IC_{50}$=0.24 μM), the first orally available non-peptidic BACE-1 inhibitor with potent Aβ-lowering effect in animals, that has been recently withdrawn from phase I clinical trials due to off-target toxicity issues. As the adverse effects displayed by LY2811376 are completely unrelated to BACE-1 inhibition, BACE-1 remaining a viable target in the search for disease-modifying anti-Alzheimer drugs, compounds $(-)$-$(I_b)$ and $(+)$-$(I_b)$ emerge as a promising non-peptidic inhibitors of BACE-1 for AD treatment.

Example 24

Aβ$_{1-42}$ Self-Aggregation Inhibition Assay

As reported in a previously published protocol (cf. M. Bartolini et al., "Insight into the Kinetic of Amyloid Beta (1-42) Peptide Self-Aggregation: Elucidation of Inhibitors' Mechanism of Action. *ChemBioChem* 2007, vol. 8, pp. 2152-2161), HFIP pretreated Aβ$_{1-42}$ samples (Bachem AG, Switzerland) were solubilized with a $CH_3CN$/0.3 mM $Na_2CO_3$ 250 mM NaOH (48.4:48.4:3.2) mixture to obtain a 500 μM solution. Experiments were performed by incubating the peptide in 10 mM phosphate buffer (pH=8.0) containing 10 mM NaCl, at 30° C. for 24 h (final Aβ concentration 50 μM) with and without inhibitor (10 μM, Aβ/inhibitor=5/1). Blanks containing the tested inhibitors were also prepared and tested. To quantify amyloid fibrils formation, the thioflavin T fluorescence method was used (cf. H. Naiki et al., "Kinetic Analysis of Amyloid Fibril Polymerization in Vitro", *Lab. Invest.* 1991, vol. 65, pp. 104-110). After incubation, samples were diluted to a final volume of 2.0 mL with 50 mM glycine-NaOH buffer (pH 8.5) containing 1.5 μM thioflavin T. A 300-second-time scan of fluorescence intensity was carried out a ($\lambda_{exc}$=446 nm; $\lambda_{em}$=490 nm, FP-6200 fluorometer, Jasco Europe), and values at plateau were averaged after subtracting the background fluorescence of 1.5 μM thioflavin T solution. The fluorescence intensities were compared and the percent inhibition due to the presence of the inhibitor was calculated by the following formula: 100−($IF_i$/$IF_o$×100) where $IF_i$ and $IF_o$ are the fluorescence intensities obtained for Aβ$_{1-42}$ in the presence and in the absence of inhibitor, respectively.

The results of the inhibition of the Aβ self-aggregation by the hydrochlorides of racemic and enantiopure huprine Y, and the hydrochlorides of racemic compounds of formula $(I_a)$-$(I_e)$ and enantiopure compounds $(-)$-$(I_b)$ and $(+)$-$(I_b)$ are summarized in Table 1.

The compounds of formula $(I_a)$-$(I_e)$ and $(-)$-$(I_b)$ and $(+)$-$(I_b)$ significantly inhibit the self-induced Aβ aggregation when tested at a 5-fold lower concentration relative to Aβ, with percentages of inhibition ranging from 32% to 43%, in all cases higher than that of the parent huprine Y.

Example 25

ACNE-Induced Aβ$_{1-40}$ Aggregation Inhibition Assay

The ability of compounds $(I_a)$-$(I_e)$ and $(-)$-$(I_b)$ and $(+)$-$(I_b)$ to inhibit the AChE-induced Aβ aggregation was assessed by using a thioflavin T fluorescence method (cf. M. Bartolini et al., "β-Amyloid Aggregation Induced by Human Acetylcholinesterase: Inhibition Studies", *Biochem. Pharmacol.* 2003, vol. 65, pp. 407-416). Thioflavin T (Basic Yellow 1), human recombinant AChE lyophilized powder, and 1,1,1,3,3,3-hexafluoro-2-propanol (HFIP) were purchased from Sigma Chemicals. Absolute DMSO over molecular sieves was from Fluka. Water was deionised and doubly distilled. Aβ$_{1-40}$, supplied as trifluoroacetate salt, was purchased from Bachem AG (Germany). Aβ$_{1-40}$ (2 mg mL$^{-1}$) was dissolved in HFIP, lyophilized, and then resolubilized in DMSO to get a 2.3 mM Aβ$_{1-40}$ solution. 1 mM Solutions of tested inhibitors were prepared by dissolution in MeOH.

Aliquots of 2 μL Aβ$_{1-40}$ peptide were incubated for 24 h at room temperature in 0.215 M sodium phosphate buffer (pH 8.0) at a final concentration of 230 μM. For co-incubation experiments aliquots (16 μL) of hAChE (final concentration 2.30 μM, Aβ/AChE molar ratio 100:1) and AChE in the presence of 2 μL of the tested inhibitor (final inhibitor concentration 100 μM) in 0.215 M sodium phosphate buffer pH 8.0 solution were added. Blanks containing Aβ$_{1-40}$ alone, human recombinant AChE alone, and Aβ$_{1-40}$ plus tested inhibitors in 0.215 M sodium phosphate buffer (pH 8.0) were prepared. The final volume of each vial was 20 μL. Each assay was run in duplicate. To quantify amyloid fibril formation, the thioflavin T fluorescence method was then applied (cf. H. Naiki et al., "Kinetic Analysis of Amyloid Fibril Polymerization in Vitro", *Lab. Invest.* 1991, vol. 65, pp. 104-110). The fluorescence intensities due to β-sheet conformation were monitored for 300 s at $\lambda_{em}$=490 nm ($\lambda_{exc}$=446 nm). The percent inhibition of the AChE-induced aggregation due to the presence of the tested compound was calculated by the following expression: 100−($IF_i$/$IF_o$×100) where $IF_i$ and $IF_e$ are the fluorescence intensities obtained for Aβ plus AChE in the presence and in the absence of inhibitor, respectively, minus the fluorescence intensities due to the respective blanks.

The results of the inhibition of the AChE-induced Aβ$_{1-40}$ aggregation by the hydrochlorides of racemic and enantiopure huprine Y, and the hydrochlorides of racemic compounds of formula $(I_a)$-$(I_e)$ and enantiopure compounds $(-)$-$(I_b)$ and $(+)$-$(I_b)$ are summarized in Table 1 below.

It should be noted that these assays are performed using high concentrations of AChE, Aβ and inhibitor. As it is explained by D. Muñoz-Torrero, on page 2451 *Curr. Med. Chem.* 2008, vol. 15, pp. 2433-2455, if one considers the inhibitor/AChE concentration ratio in both the Ellman's assay for determination of the AChE inhibitory activity and in the thioflavin T-based fluorimetric assay for determination of the inhibitory activity on the AChE-induced Aβ aggregation, the resulting values are indeed of the same magnitude. Thus, it seems reasonable that similar amounts of a given inhibitor might lead to both inhibitory activities.

The compounds of formula $(I_a)$-$(I_e)$ and $(-)$-$(I_b)$ and $(+)$-$(I_b)$ significantly inhibit, at a 100 μM concentration, the hAChE-induced Aβ aggregation, with percentages of inhibition ranging from 29% to 49% (Table 1), in all cases higher than that of the parent huprine Y.

In Table 1, values are expressed as mean±standard error of the mean from two independent measurements, each performed in duplicate. To determine the inhibitory activity of the AChE-induced $A\beta_{1-40}$ aggregation a 100 μM concentration of the inhibitor was used. To determine the inhibitory activity of the $A\beta_{1-42}$ self-induced aggregation a 10 μM concentration of the inhibitor was used ([Aβ]/[I]=5/1). Nd means not determined.

TABLE 1

| Compound | BACE-1 $IC_{50}$ μM | AChE-induced $A\beta_{1-40}$ aggregation (%) | $A\beta_{1-42}$ self-induced aggregation (%) |
|---|---|---|---|
| (±)-($I_a$)•HCl | 0.98 ± 0.2 | 44.7 ± 8.4 | 33.1 ± 5.4 |
| (±)-($I_b$)•HCl | 0.12 ± 0.1 | 48.7 ± 8.4 | 38.0 ± 4.6 |
| (−)-($I_b$)•HCl | 0.08 ± 0.01 | 38.1 ± 0.7 | 43.2 ± 4.7 |
| (+)-($I_b$)•HCl | 0.08 ± 0.01 | 36.9 ± 3.4 | 38.4 ± 5.5 |
| (±)-($I_c$)•HCl | 1.19 ± 0.2 | 29.2 ± 2.4 | 40.9 ± 4.4 |
| (±)-($I_d$)•HCl | 1.20 ± 0.1 | 38.2 ± 2.6 | 35.3 ± 4.0 |
| (±)-($I_e$)•HCl | 2.02 ± 0.4 | 35.2 ± 1.8 | 32.4 ± 3.6 |
| (±)-Huprine Y•HCl | nd | 17.1 ± 4.5 | nd |
| (−)-Huprine Y•HCl | >5 (14.0 ± 0.1% at 5 μM) | 24.7 ± 1.3 | 11.5 ± 5.2 |
| (+)-Huprine Y•HCl | >5 (13.6 ± 2.3% at 5 μM) | 9.1 ± 3.6 | 13.2 ± 1.9 |

Example 26

AChE and BChE Inhibition Assay

AChE inhibitory activity of compounds $(I_a)$-$(I_e)$ and $(-)$-$(I_b)$ and $(+)$-$(I_b)$ was evaluated spectrophotometrically at 25° C. by the method of Ellman et al., using recombinant human AChE (hAChE) and *Electrophorus electricus* (ee) AChE and acetylthiocholine iodide as substrate (cf. G. L. Ellman et al., "New and Rapid Colorimetric Determination of Acetylcholinesterase Activity" *Biochem. Pharmacol.* 1961, vol. 7, pp. 88-95). For eeAChE inhibitory activity determination, the reaction took place in a final volume of 300 μL of 0.1 M phosphate-buffered solution pH 8.0, containing 0.03 unit/mL of ee AChE and 333 μM 5,5'-dithiobis(2-nitrobenzoic) acid (DTNB) solution used to produce the yellow anion of 5-thio-2-nitrobenzoic acid. Inhibition curves were performed in duplicates using at least 10 increasing concentrations of inhibitor and preincubating at 37° C. for 20 min. One duplicate sample without inhibitor was always present to yield 100% of AChE activity. Then, substrate acetylthiocholine (450 μM) was added and the reaction was developed at 37° C. for 5 min. The color production was measured at 414 nm.

BChE inhibitory activity determinations were carried out similarly by the method of Ellman et al., using 0.02 unit/mL of human serum BChE and 300 μM butyrylthiocholine, instead of AChE and acetylthiocholine, in a final volume of 300 μL.

Data from concentration-inhibition experiments of the inhibitors were calculated by non-linear regression analysis, using the GraphPad Prism program package (GraphPad Software; San Diego, USA), which gave estimates of the $IC_{50}$ (concentration of drug producing 50% of enzyme activity inhibition). Results are expressed as mean±S.E.M. of at least 4 experiments performed in duplicate. DTNB, acetylthiocholine, butyrylthiocholine, and enzymes were purchased from Sigma.

For hAChE inhibitory activity determination, initial rate assays were performed at 37° C. with a Jasco V-530 double beam spectrophotometer. Stock solutions of the tested compounds (1 mM) were prepared in methanol and diluted in methanol. The assay solution consisted of a 0.1 M phosphate buffer, pH 8.0, with the addition of 340 μM DTNB, 0.02 unit/mL human recombinant AChE (Sigma Chemical, St. Louis, Mo.), and 550 μM substrate (acetylthiocholine iodide). Assay solutions with and without inhibitor were preincubated at 37° C. for 20 min followed by the addition of substrate. Blank solutions containing all components except AChE were prepared in parallel to account for the non-enzymatic hydrolysis of the substrate. Five increasing concentrations of the inhibitor were used, able to give an inhibition of the enzymatic activity in the range of 20-80%. The results were plotted by placing the percentage of inhibition in function of the decimal log of the final inhibitor concentration. Linear regression and $IC_{50}$ values were calculated using Microcal Origin 3.5 software (Microcal Software, Inc).

The results obtained are summarized in Table 2. It includes AChE and BChE inhibitory activities of rhein and the hydrochlorides of racemic and enantiopure huprine Y as reference compounds, and the hydrochlorides of compounds $(I_a)$-$(I_e)$ and $(-)$-$(I_b)$ and $(+)$-$(I_b)$. The values are expressed as mean±standard error of the mean of at least four experiments. $IC_{50}$ inhibitory concentration (nM) of recombinant human AChE, *Electrophorus electricus* AChE or human serum BChE activity.

TABLE 2

| | $IC_{50}$ (nM) | | |
|---|---|---|---|
| compound | eeAChE | hAChE | hBChE |
| (±)-($I_a$)•HCl | 88.6 ± 6.7 | 4.4 ± 0.2 | 350 ± 17 |
| (±)-($I_b$)•HCl | 32.6 ± 1.7 | 3.6 ± 0.2 | 620 ± 24 |
| (−)-($I_b$)•HCl | 9.4 ± 1.6 | 2.4 ± 0.2 | 513 ± 58 |
| (+)-($I_b$)•HCl | 98.9 ± 14.2 | 2930 ± 285 | 265 ± 21 |
| (±)-($I_c$)•HCl | 46.7 ± 2.4 | 7.6 ± 0.4 | 1100 ± 40 |
| (±)-($I_d$)•HCl | 16.3 ± 2.3 | 17.4 ± 2.2 | 645 ± 67 |
| (±)-($I_e$)•HCl | 60.0 ± 7.5 | 18.2 ± 2.2 | 510 ± 20 |
| Rhein | 637 ± 87 | >10000 | 17000 ± 4220 |
| (±)-Huprine Y•HCl | 0.08 ± 0.01 | 0.69 ± 0.03 | 181 ± 15 |
| (−)-Huprine Y•HCl | 0.06 ± 0.01 | 0.43 ± 0.03 | 222 ± 17 |
| (+)-Huprine Y•HCl | 373 ± 50 | 13.6 ± 1.50 | 170 ± 17 |

Compounds $(I_a)$-$(I_e)$ and $(-)$-$(I_b)$ and $(+)$-$(I_b)$ are potent inhibitors of hAChE and eeAChE and moderately potent inhibitors of hBChE, exhibiting $IC_{50}$ values in the low and medium nanomolar range, respectively. All the compounds are clearly more potent eeAChE inhibitors than the parent rhein but less potent than the parent (±)-huprine Y.

Example 27

In Vivo Studies in *Escherichia coli* Overexpressing Aβ42 and Tau Protein

Cloning and Overexpression of Aβ42 Peptide:
*Escherichia coli* BL21 (DE3) competent cells were transformed with pET28 vector (Novagen, Inc., Madison, Wis., USA) encoding the sequence for Aβ42 as insert. Because of the addition of the initiation codon ATG in front of both genes, the overexpressed peptide contains an additional methionine residue at its N terminus. For overnight culture preparation, 10 mL of lysogeny broth (LB) medium containing 50 µg·mL$^{-1}$ of kanamycin were inoculated with a colony of BL21 (DE3) bearing the plasmid to be expressed at 37° C. After overnight growth, the OD$_{600}$ is usually 2-2.5. For expression of Aβ42 peptide, 20 µL of overnight culture are transferred into eppendorf tubes of 1.5 mL containing 980 µL of LB medium with 50 µg·mL$^{-1}$ of kanamycin, 1 mM of isopropyl 1-thio-β-D-galactopyranoside (IPTG) and 10 µM of each testable drug in DMSO. The samples were grown for 24 h at 37° C. and 1400 rpm using a Thermomixer (Eppendorf, Hamburg, Germany). In the negative control (without drug) the same amount of DMSO was added in the sample.

Cloning and Overexpression of Tau Protein:

*Escherichia coli* BL21 (DE3) competent cells were transformed with pTARA containing the RNA-polymerase gen of T7 fag (T7RP) under the control of the promoter P$_{BAD}$). *Escherichia coli* BL21 (DE3) with pTARA competent cells were transformed with pRKT42 vector encoding four repetitions of tau protein in two inserts. For overnight culture preparation, 10 mL of M9 medium containing 0.5% of glucose, 50 µg·mL$^{-1}$ of ampicillin and 12.5 µg·mL$^{-1}$ of chloramphenicol were inoculated with a colony of BL21 (DE3) bearing the plasmids to be expressed at 37° C. After overnight growth, the OD$_{600}$ is usually 2-2.5. For expression of tau protein, 20 µL of overnight culture are transferred into eppendorf tubes of 1.5 mL containing 980 µL of M9 medium containing 0.25% of arabinose, 50 µg·mL$^{-1}$ of ampicillin and 12.5 µg·mL$^{-1}$ of chloramphenicol and 10 µM of each testable drug in DMSO. The samples were grown for 24 h at 37° C. and 1400 rpm using a Thermomixer (Eppendorf, Hamburg, Germany). In the negative control (without drug) the same amount of DMSO was added in the sample.

Thioflavin-S (Th-S) Steady-State Fluorescence:

Th-S (T1892) and other chemical reagents were purchased from Sigma (St. Louis, Mo.). Th-S stock solution (250 mM) was prepared in double-distilled water purified through a Milli-Q system (Millipore, USA). Fluorescent spectral scans of Th-S were analyzed using an Aminco Bowman Series 2 luminescence spectrophotometer (Aminco-Bowman AB2, SLM Aminco, Rochester, N.Y.). For the fluorescence assay, 25 µM of Th-S (20 µL of Th-S in 180 µL of sample) were added to samples and spectra were recorded after 15 min equilibration at 37° C. Excitation and emission slit widths of 5 nm were used. Finally, the fluorescence emission at 520 nm, when exciting at 440 nm, was recorded. In order to normalize the Th-S fluorescence as a function of the bacterial concentration OD$_{600}$ was obtained using a Shimadzu UV-2401 PC UV-Vis spectrophotometer (Shimadzu, Japan). Note that the fluorescence normalization has been carried out considering as 100% the Th-S fluorescence of the bacterial cells expressing the peptide or protein in absence of drug and 0% the Th-S fluorescence of the bacterial cells non-expressing the peptide or protein.

Figure 2:
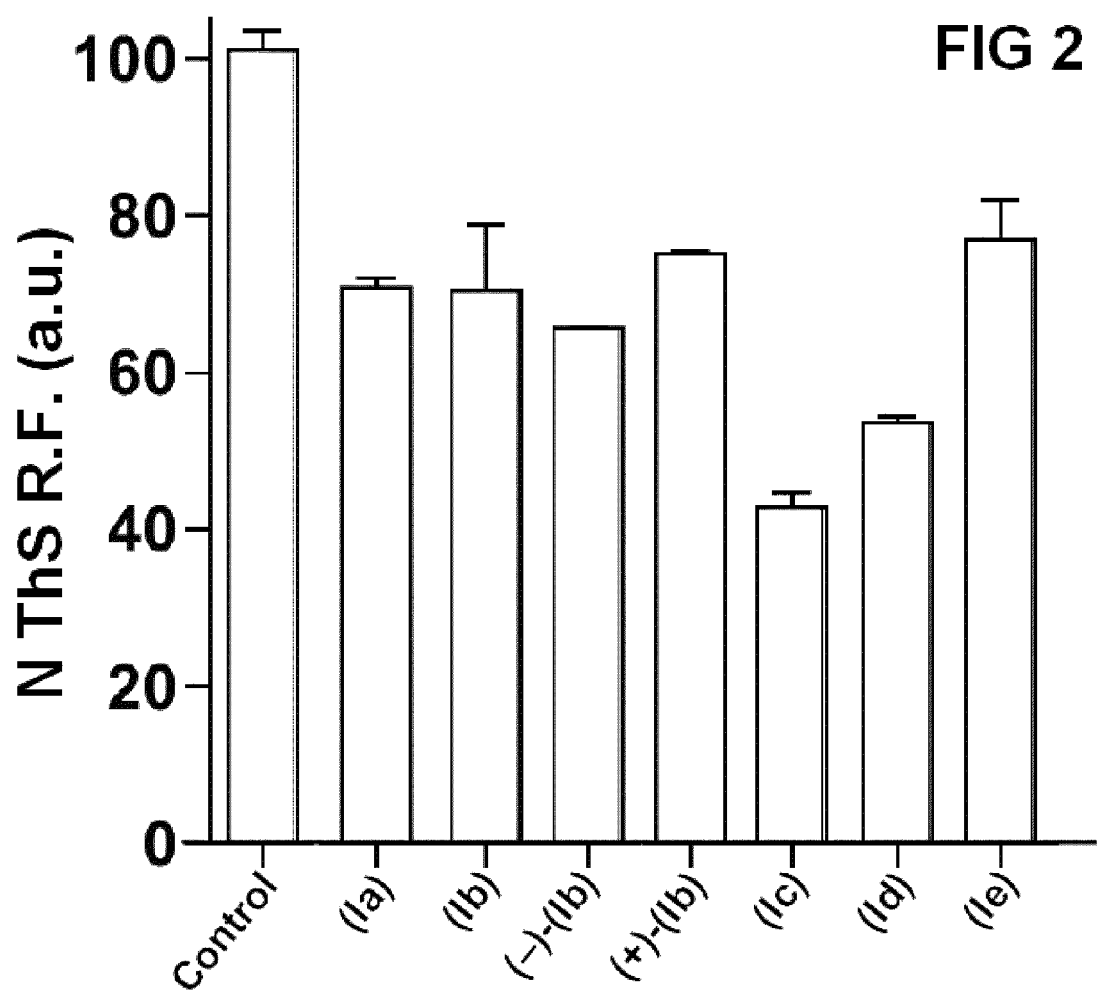
FIG. 2 shows the normalized thioflavin-S (Th-S) fluorescence in samples of *Escherichia coli* BL21 (DE3) overexpressing tau protein in the absence and in the presence of compounds of formula $(I_a)$-$(I_e)$, (−)-$(I_b)$ and (+)-$(I_b)$, as a measure of their effect on tau protein aggregation.

Compounds (I$_a$)-(I$_e$) and (−)-(I$_b$) and (+)-(I$_b$) exhibit a significant Aβ42 (FIG. 1) and tau protein (FIG. 2) anti-aggregating activity. All the compounds are clearly more potent inhibitors of Aβ42 and tau protein aggregation than (±)-huprine Y and roughly equipotent to rhein (data not shown).

Examples 28-33

In Vivo Studies in APP-PS1 Mice

Animals and Treatment:

APPswe/PSENΔE9 double transgenic mice, which express the mutant APPswe (K595N/M596L) and PSEN1ΔE9, the deletion of the exon 9 under the control of the mouse prion promoter, were obtained from the Jackson Laboratory (Bar Harbor, Me., USA, Stock no 004462). Experimental design comprised 6 groups. Treatment started when mice were 6 months old and when another set was 10 months old and continued for 4 weeks (so, at the end of the treatment, mice were 7 and 11 months old, respectively). Each set comprised three experimental groups: Tg Control, Tg+(−)-(I$_b$) (in the drawings referred to as H9A(−)) and Tg+(+)-(I$_b$) (in the drawings referred to as H9A(+)). The treatment consisted of intraperitoneal injection three times per week for 4 weeks. The injectable (I$_b$) solution (0.1 mM) was prepared in DMSO (20%) in saline serum (NaCl 0.9%). 4 µl of this solution was injected per gram of weight.

Primary Antibodies Used:

Rabbit anti-GFAP (DAKO, Carpinteria, Calif.), mouse anti-Aβ (4G8, Chemicon, Temecula, Calif.), mouse monoclonal anti-PSD95, K28/43 clone and Vglut-1, obtained from Antibodies, Inc. (UC Davis/NIH NeuroMab Facility, Davis, Calif.), mouse anti-GluA2 (clone L21/32; UC Davis/NIH NeuroMab Facility) and goat anti-synaptophysin (sc-7568 Santa Cruz Biotechnology, Inc.).

Slice Preparation and Electrophysioloqy:

Hippocampal slices were prepared according to standard procedures previously described. Briefly, transverse slices (350 µm) from the dorsal hippocampus were cut under cold artificial cerebrospinal fluid (ACSF, in mM: 124 NaCl, 2.6 NaHCO$_3$, 10 D-glucose, 2.69 KCl, 1.25 KH$_2$PO$_4$ 2.5 CaCl$_2$, 1.3 MgSO$_4$, and 2.60 NaHPO4) using a Vibratome (Leica VT 1000 s, Germany) and incubated in ACSF for 1 h at room temperature. In all experiments, 10 µM picrotoxin (PTX) was added to suppress inhibitory GABAA transmission. Slices were transferred to an experimental chamber (2 mL), superfused (3 mL/min, at 20-22° C.) with gassed ACSF and visualized by trans-illumination with a binocular microscope (MSZ-10, Nikon, Melville, N.Y.). To evoke field excitatory postsynaptic potentials (fEPSPs), we stimulate with bipolar concentric electrodes (Platinum/Iridium, 125 µm OD diameter, FHC Inc., Bowdoin, Me.) generated by a stimulator (Axon 700b, Molecular Devices, Sunnyvale, Calif.) and connected to an isolation unit (Isoflex, AMPI, Jerusalem, Israel). The stimulation was in the Stratum Radiatum within 100-200 µm from the recording site. The paired pulse facilitation index was calculated by ((R2−R1)/R1), where R1 and R2 were the peak amplitudes of the first and second fEPSP respectively. To generate LTP we used Theta Burst Stimulation (TBS) consisting of 5 trains of stimulus with an inter-train interval of 20 s. Each train consisted of 10 bursts at 5 Hz and each burst having 4 pulses at 100 Hz. To generate LTD we used Low Frequency Stimulation (LFS) consisting in 900 paired pulses at 1 Hz. Recordings were filtered at 2.0-3.0 kHz, sampled at 4.0 kHz using an A/D converter, and stored with pClamp 10 (Molecular Devices). Evoked postsynaptic responses were analyzed off-line, using an analysis software (pClampfit, Molecular Devices), which allowed visual detection of events, computing only those events that exceeded and arbitrary threshold.

Immunoblotting:

The hippocampus of treated or control transgenic mice were dissected on ice and immediately frozen at −150° C. or processed. Briefly, hippocampal tissue were homogenized in RIPA buffer (50 mM Tris-Cl, pH 7.5, 150 mM NaCl, 1% NP-40, 0.5% sodium deoxycholate, and 1% SDS) supplemented with a protease inhibitor cocktail (Sigma-Aldrich P8340) and phosphatase inhibitors (50 mM NaF, 1 mM Na$_3$VO$_4$ and 30 µM Na$_4$P$_2$O$_7$) using a Potter homogenizator and then passed sequentially through different caliber syringes. Protein samples were centrifuged at 14000 rpm at 4° C. twice for 10 min. Protein concentration was determined using the BCA Protein Assay Kit (Pierce Biotechnology, Rockford, Ill.). 20 and 40 micrograms of hippocampal samples were resolved by 10% SDS-PAGE, transferred to a PVDF membrane. The reactions were followed by incubation with primary antibodies, secondary antibodies anti-mouse, anti-goat or anti-rabbit IgG peroxidase conjugated (Pierce) and developed using an ECL kit (Western Lightning Plus ECL, Perkin Elmer).

Behavioral Test. Memory Flexibility Test:

The Morris Water Maze (MWM) was performed. Briefly, mice were trained in a circular water maze of 1.2 m diameter (opaque water, 50 cm deep, 19-21° C., 9-cm platform 1 cm below water, maximum trial duration 60 s, 10 s on platform at the end of trials). Each animal was trained for one pseudo-random location of the platform per day, for 4 days, with a new platform location each day. Training was conducted up to 10 trials per day, until the criterion of 3 successive trials with an escape latency of <20 s was met. On completion of testing, the mouse was removed from the maze, dried and returned to its cage. The animals were tested for the next location on the following day. Data were collected using a video tracking system for water maze (HVS Imagen).

Immunohistochemical Procedures:

Perfusion, fixation and free-floating immuno-cytochemical procedures were performed as previously described. Washing and dilution of immune-reagents were performed using 0.01 M PBS with 0.2% Triton X-100 (PBS-T) throughout experiments, with two PBS-T washes per antibody incubation. Sections were pretreated with 0.5% $H_2O_2$ for 30 min to reduce endogenous peroxidase activity followed by treatment with 3% bovine serum albumin (BSA) at room temperature for 1 h to avoid non-specific binding. Primary antibodies (anti-Aβ, 4G8 and anti-GFAP) were incubated overnight at 4° C. Detection of primary antibody was performed using the Pierce ABC Kit (Thermo Fisher Scientific Inc., Rockford, Ill.). Staining was developed by incubating for 15 min with 0.6% diaminobenzidine followed by the addition of $H_2O_2$ (0.01% final concentration). After immunostaining, all sections were mounted on gelatin-coated slides, air-dried, dehydrated and cover-slipped with Canada balsam (Merck, Darmstadt, Germany).

Thioflavin-S (Th-S) Staining:

Th-S staining was developed on gelatin-coated slices as previously described. After dehydration and rehydration in ethanol and xilol batteries, slices were incubated in distilled water for 10 min and then were immersed in the Th-S solution (0.1% ThS in 70% ethanol) for 5 min. Slices were then washed twice in 70% ethanol for 30 s and cover-slipped with antifade mounting medium in dark.

Image Analysis:

Stained brain sections were photographed using an Olympus BX51 microscope coupled to a Micro-publisher 3.3 RTV camera (QImaging). The luminescence of the incident light and the time of exposure were calibrated to assign pixel values ranging from 0 to 255 in RGB image (no-light to full-light transmission), which were used along all preparations. The images were loaded into ImageJ v.1.40 g software (NIH) for analysis. Selection of areas for measurement was performed by manual threshold adjustment or by direct manual selection of ROIs in heterogeneous stains.

Statistical Analysis:

Results are expressed as mean±standard error. Data were analyzed by one-way ANOVA, followed by Bonferroni's post hoc test. $p \leq 0.05$ was considered as statistically significant. Statistical analysis was performed using Prism software (GraphPad Software Inc.).

Example 28

Electrophysiological Assays in Hippocampal Slices Incubated with Aβ Oligomers and (−)-($I_b$) or (+)-($I_b$)

Electrophysiological registers of hippocampal slices of 2-month-old C57bl6 male mice were assessed to evaluate the synaptic transmission through the long-term potentiation (LTP). Hippocampal slices were incubated with Aβ oligomers 10 min prior and 10 min after LTP induction. No induction of LTP was observed in the presence of Aβ oligomers (FIG. 3A, white circles). Similarly, there was no LTP induction observed with (−)-($I_b$) (FIG. 3A, light grey circles). On the contrary, treatment with (+)-($I_b$) (FIG. 3A, dark grey circles), where a 200% LTP induction was observed, showed a similar effect to that seen in control slices treated only with ACSF solution. In FIG. 3B, the quantification at min 60 of fEPSP are shown. Compound (+)-($I_b$) reached a 200% magnitude response when compared to slices treated with Aβ oligomers or Aβ oligomers+(−)-($I_b$). In conclusion, (+)-($I_b$) protects against the synaptic failure induced by acute treatments with Aβ oligomers, within the context of LTP induction.

Example 29

Synaptic Protein Levels of Hippocampal Slices Incubated with (−)-($I_b$) or (+)-($I_b$), in the Presence of Aβ Oligomers In FIG. 4, changes were observed in synaptic protein levels of brain slices of 2-month-old C57bl6 mice treated with Aβ oligomers and different concentrations of (−)-($I_b$) (FIG. 4A) and (+)-($I_b$) (FIG. 4B) for 1 h. Densitometric analysis of western blots showed that the subunit GluA2 of the AMPA receptor (GluR2 in the drawing), PSD95 (a scaffold protein within the post-synaptic density), the vesicular glutamate transporter 1 (VGlut1) and synaptotagmin (SYN, a pre-synaptic protein mainly present in exocytic vesicles), diminished after Aβ oligomers treatment (black bars) in comparison with control slices (white bars), whereas synaptophysin (SYP), a pre-synaptic protein, did not show variation. In slices co-treated with (−)-($I_b$) (FIG. 4A), the neuroprotective effect of the compound was observed. In the case of GluA2 and PSD95 we noticed an evident effect at 10 and 100 μM and in the case of VGlut1 we observed an increment for every concentration of the compound that was used. However, for SYP no effects were observed. In the case of (+)-($I_b$) (FIG. 4B), GluA2, PSD95 and SYN showed increased levels of total protein with every concentration used, while VGlut1 and SYP showed no changes. In conclusion, the treatment with compounds (−)-($I_b$) and (+)-($I_b$) prevents the loss of proteins within the post-synaptic region, caused by Aβ oligomers, these data being consistent with the effects seen in FIG. 3.

Example 30

Effects of (−)-($I_b$) and (+)-($I_b$) Over Cognitive Failure

Cognitive failure of APP-PS1 mice was evaluated through a variant of the Morris water maze, called the Memory flexibility test, which measures episodic and spatial memory.

Figure 5:
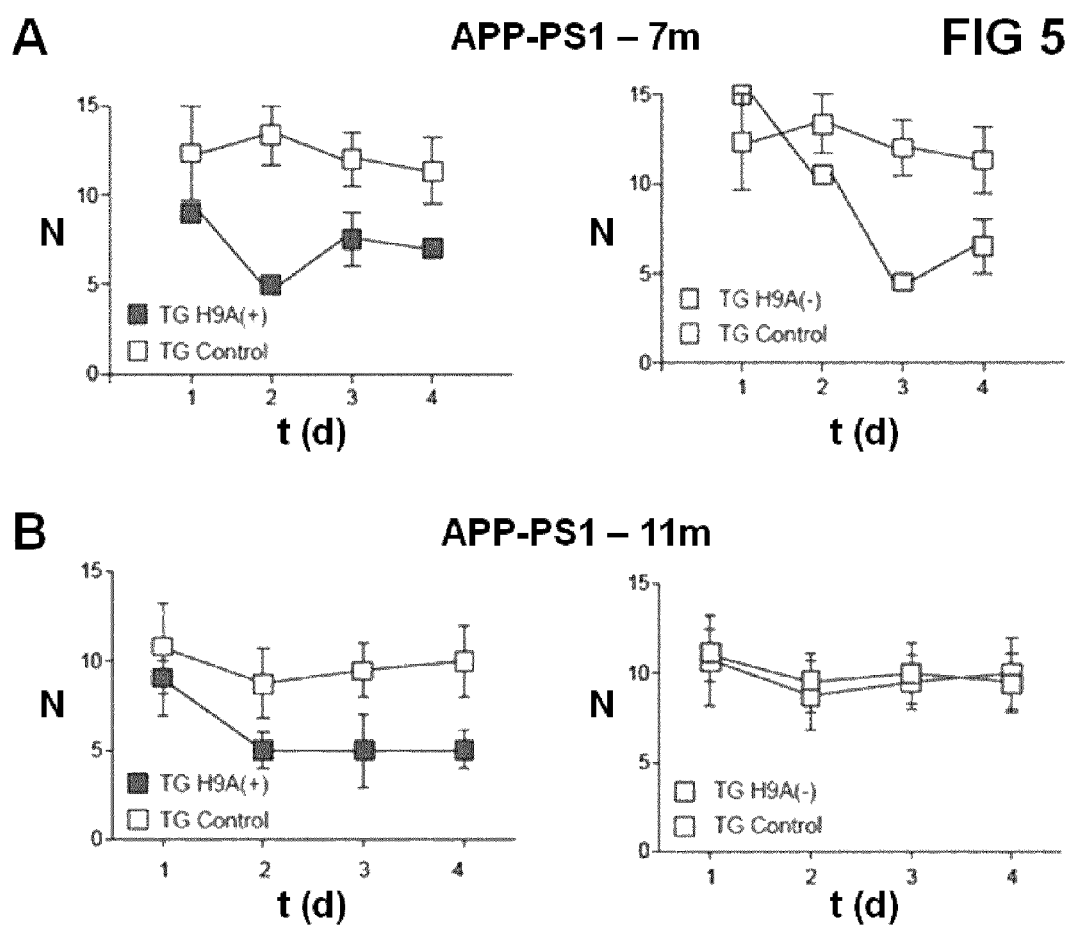
FIG. 5 shows the effects of compounds of formula (−)-$(I_b)$ and (+)-$(I_b)$ on the cognitive failure of APP-PS1 mice, using the memory flexibility test.

This test consists of the animals finding a hidden platform in a pool containing opaque water, with only the help of visual cues. In this test, the animals must find the hidden platform three times in a row and under 20 s each time to consider that they learned where to find the platform (in the drawing, it is represented as the number of trials that the animal took to reach criteria). In FIG. 5A where the animal conduct was analyzed in 7-month-old transgenic mice, we observed that untreated animals take about 12-13 trials to reach criteria while 7-month-old APP-PS1 animals treated with (+)-($I_b$) took an average of 7 trials to reach criteria. Animals treated with (−)-($I_b$) showed improved behavior within days. In the case of 11-month-old APP-PS1 animals (FIG. 5B) an improvement in the cognitive abilities was observed in animals treated with (+)-($I_b$), who took less trials to reach learning criteria. With the (−)-($I_b$) treatment there was no significant change when compared with untreated APP-PS1 animals. In summary, both compounds prevent the loss of cognitive abilities in 7-month-old animals, but only (+)-($I_b$) prevents memory loss in 11-month-old animals.

Example 31

Electrophysiology Studies in Hippocampal Slices from APP-PS1 Mice Treated with (−)-($I_b$) or (+)-($I_b$)

Figure 6:
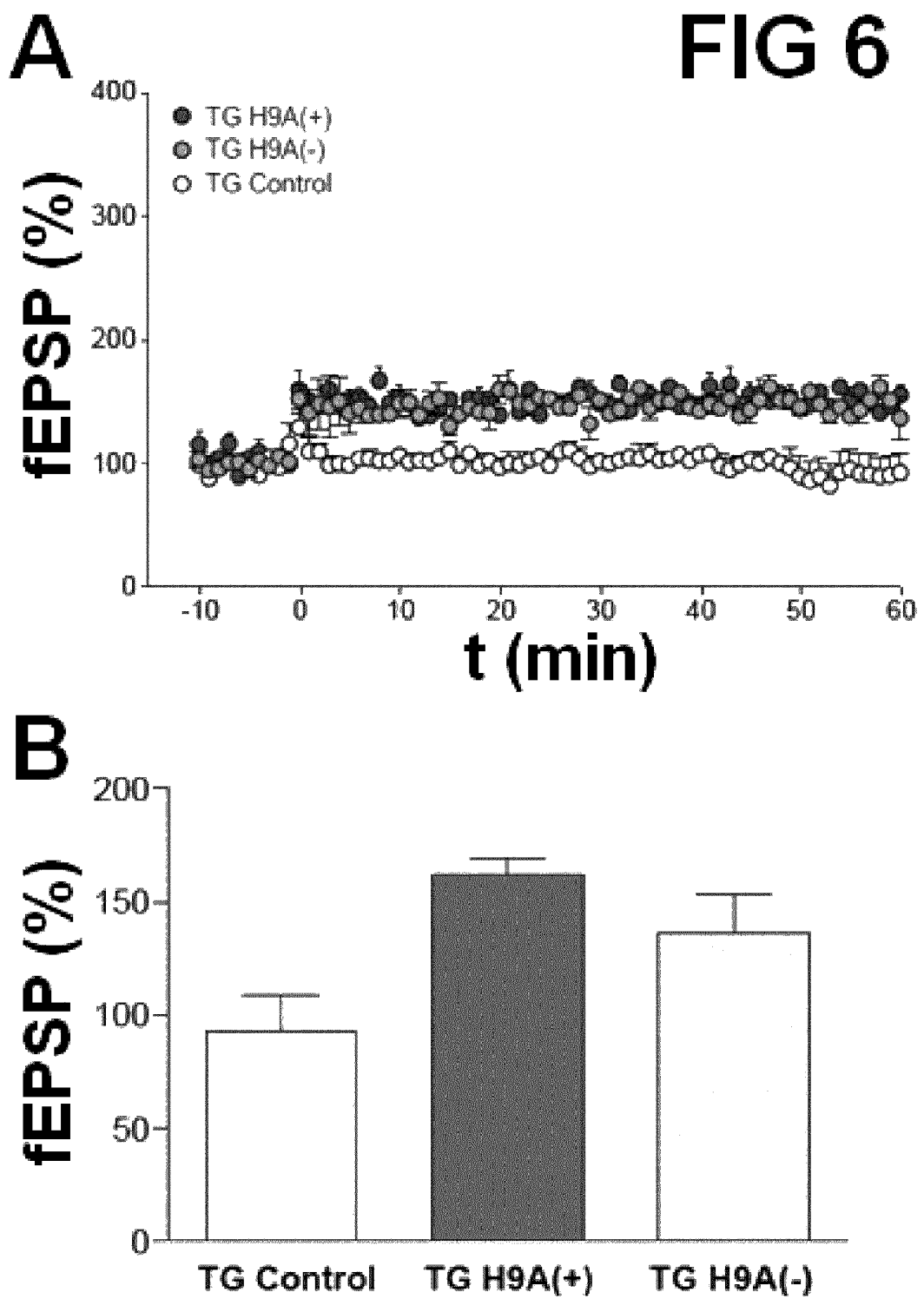
FIG. 6 shows the results of electrophysiology studies in hippocampal slices of APP-PS1 mice treated with compounds of formula (−)-$(I_b)$ and (+)-$(I_b)$.

The integrity of synaptic plasticity was evaluated in APP-PS1 control and (−)-($I_b$) or (+)-($I_b$) treated mice. In order to do so, LTP induction protocols were used to assess a correlation of processes associated with memory and learning. Electrophysiological recordings of fEPSP in CA3-CA1 hippocampal areas and the fEPSP slope were carried out. In the case of control transgenic mice there was no LTP induction, which is consistent with previous publications (FIG. 6A, white circles). However, animals treated with both (+)-($I_b$) and (−)-($I_b$) were able to generate LTP, which was sustained over time (FIG. 6, black and grey circles respectively). This phenomenon was quantified at 60 min and it is evident that both compounds reached a 150% magnitude when compared with untreated brain slices. We can conclude that (−)-($I_b$) and (+)-($I_b$) protect from synaptic failure in the APP-PS1 mouse model of AD and can restore memory and learning processes associated with synaptic plasticity.

Example 32

Effect of (−)($I_b$) and (+)($I_b$) on Amyloid Neuropathology in APP-PS1 Mice

Figure 7:
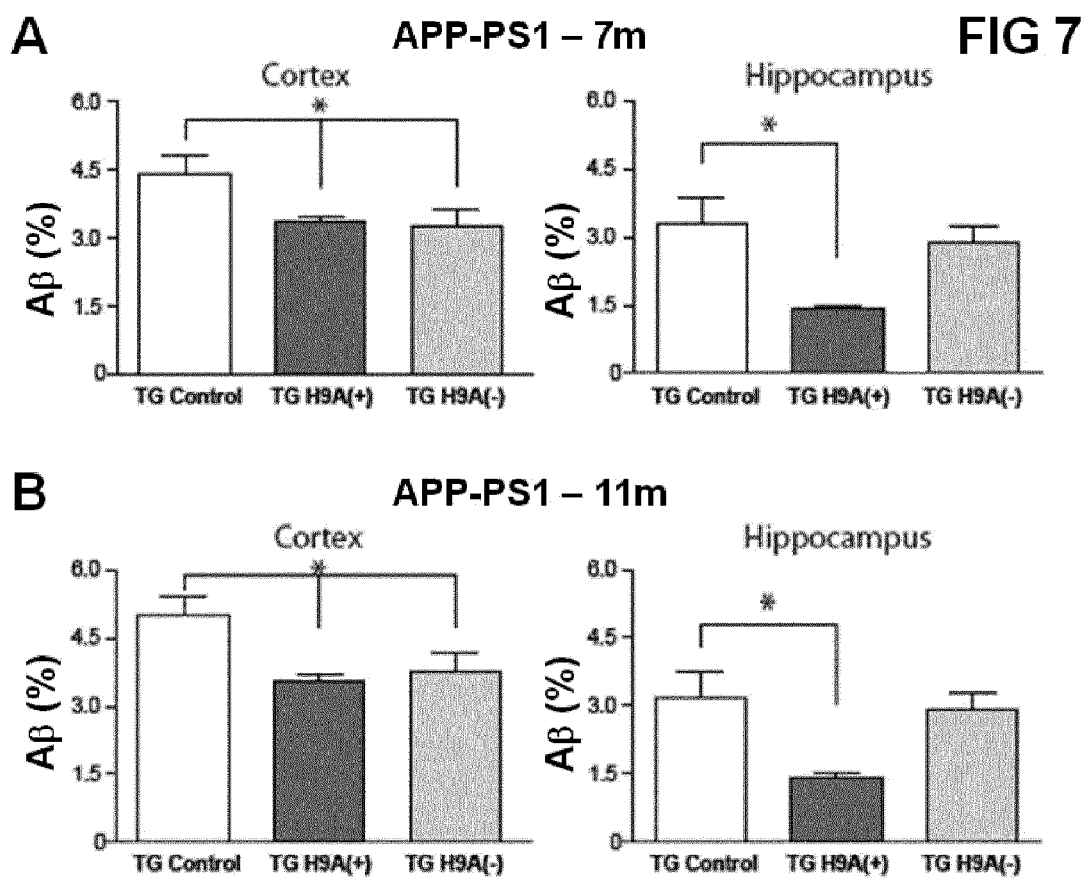
FIG. 7 shows the total load of brain amyloid deposits present in 6- and 11-month-old APP-PS1 mice treated with compounds of formula (−)-$(I_b)$ and (+)-$(I_b)$, using Aβ 6E10 immunodetection.

The animal model used here presents histopathological lesions that are hallmark features of AD such as senile plaques. To determine whether the improvement in behavior tests correlated with a change in neuropathological markers of AD, the total load of amyloid deposits present in APP-PS1 mice was analyzed. Brain slices obtained from control transgenic mice and (−)-($I_b$) and (+)-($I_b$) treated transgenic mice underwent Aβ 6E10 immunodetection and total load of Aβ deposits were analyzed. Brains from 7-month-old animals treated with either compound showed a significant reduction in the percentage of Aβ-positive aggregate area present in the brain cortex (FIG. 7A) but only (+)-($I_b$) diminished the load levels of Aβ oligomers in the hippocampus. As for the 11-month-old APP-PS1 animals (FIG. 7B), in both treatments a reduction in total Aβ load in the cortex area was observed, while as well as the previous case, only (+)-($I_b$) shows a reduction in total load of Aβ in the hippocampus.

To analyze if the different compounds alter the amount of amyloid deposits present, brain slices of APP-PS1 control and (−)-($I_b$)- and (+)-($I_b$)-treated animals were stained with Thioflavin-S, which is a fluorescent dye that binds to β-sheet amyloid aggregates, changing its fluorescence properties. This is why we used this method to analyze the amount of senile plaques in the brain of control and (−)-($I_b$)- and (+)-($I_b$)-treated transgenic mice. Through this method the positive area fractions were analyzed (FIG. 8). This analysis showed a significant reduction in the Th-S positive area with both treatments. Within the cortex of 7-month-old mice, only (+)-($I_b$) presented a reduction in the amyloid aggregates in the hippocampal region of APP-PS1 mice while in 11-month-old transgenic mice, only (+)-($I_b$) caused a reduction in amyloid deposits, both in the cortex and hippocampus (FIG. 8B). These results show that (−)-($I_b$)- and especially (+)-($I_b$)-treatment causes a reduction in the total amount of Aβ aggregates.

Example 33

Effects of (−)-($I_b$) and (+)-($I_b$) on Neuroinflammation in APP-PS1 Mice

Neuroinflamation was evaluated, mainly through astrogliosis, in the brain of control and (−)-($I_b$)- and (+)-($I_b$)-treated APP-PS1 mice through immunostaining with anti-GFAP, which marks the intermediary filaments of astrocytes. With this and evaluating the amount of GFAP positive cells and morphology changes, it is possible to evaluate the inflammatory state caused by toxic agents. The analysis was performed through the detection of the occupied area by hyperreactive astrocytes observed in 7—(FIG. 9A) and 11—(FIG. 9B) month-old transgenic animals treated with (+)-($I_b$) and (−)-($I_b$). In every case, a decrease in the inflammatory response was observed, suggesting not only an anti-inflammatory effect, but also a decrease in Aβ oligomer aggregates.

Overall the results of the in vivo studies clearly demonstrate that (−)-($I_b$) and especially (+)-($I_b$) reduce cognitive impairment, synaptic failure and amyloid pathology in this transgenic mouse model of AD.

The invention claimed is:
1. A compound of formula (I) or a pharmaceutically acceptable salt thereof, or any stereoisomer or mixture thereof,

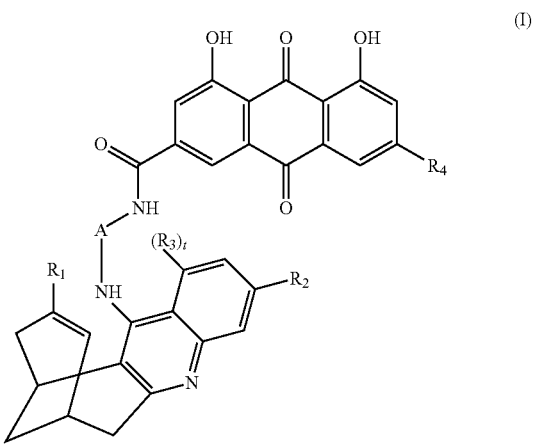

wherein:
$R_1$ is a ($C_1$-$C_2$) alkyl radical;
$R_2$ and $R_3$ are radicals independently selected from the group consisting of F, Cl and methyl;
$R_4$ is H or OH;
A is a birradical selected from the group consisting of —($CH_2$)$_n$— and —($CH_2$)-phenyl-($CH_2$)—;
t is an integer from 0 to 1; and
n is an integer from 8 to 15.

2. The compound according to claim 1, wherein $R_1$ is methyl, $R_2$ is Cl, t is 0, and $R_4$ is H.

3. The compound according to claim 1, wherein A is —$(CH_2)_n$— and n is an integer from 8 to 12.

4. The compound according to claim 3, wherein n is an integer from 8 to 9.

5. The compound according to claim 1, wherein A is —$(CH_2)$— phenyl-$(CH_2)$—.

6. The compound according to claim 1, which is selected from the following list:
- (±)-N-{8-[(3-chloro-6,7,10,11-tetrahydro-9-methyl-7,11-methanocycloocta[b]quinolin-12-yl)amino]octyl}-9,10-dihydro-4,5-dihydroxy-9,10-dioxoanthracene-2-carboxamide;
- (±)-N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide;
- (−)-(7S,11S)—N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide;
- (+)-(7R,11R)—N-{9-[(3-chloro-6,7,10,11-tetrahydro-9-methyl-7,11-methanocycloocta[b]quinolin-12-yl)amino]nonyl}-9,10-dihydro-4,5-dihydroxy-9,10-dioxoanthracene-2-carboxamide;
- (±)-N-{10-[(3-chloro-6,7,10,11-tetrahydro-9-methyl-7,11-methanocycloocta[b]quinolin-12-yl)amino]decyl}-9,10-dihydro-4,5-dihydroxy-9,10-dioxoanthracene-2-carboxamide;
- (±)-N-{11-[(3-chloro-6,7,10,11-tetrahydro-9-methyl-7,11-methanocycloocta[b]quinolin-12-yl)amino]undecyl}-9,10-dihydro-4,5-dihydroxy-9,10-dioxoanthracene-2-carboxamide; and
- (±)-N-{4-{[(3-chloro-6,7,10,11-tetrahydro-9-methyl-7,11-methanocycloocta[b]quinolin-12-yl)amino]methyl}benzyl}-9,10-dihydro-4,5-dihydroxy-9,10-dioxoanthracene-2-carboxamide.

7. The compound according to claim 1, wherein the pharmaceutically acceptable salt is a hydrochloride salt.

8. A process for the preparation of the compound of formula (I) as defined in claim 1, which comprises:
(a) reacting a compound of formula (II), a salt or a reactive derivative thereof,

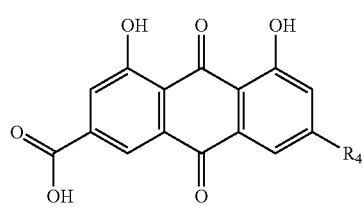

(II)

with a compound of formula (III) or a salt thereof, or any stereoisomer or mixture thereof;

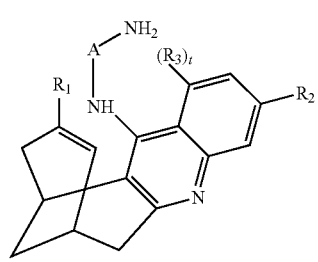

(III)

wherein $R_1$, $R_2$, $R_3$, $R_4$, A, t, and n are as defined in claim 1, respectively; and, (b) optionally, converting the compound thus obtained into a pharmaceutically acceptable salt by reacting it with a pharmaceutically acceptable acid.

9. The process according to claim 8, further comprising a previous step of submitting a compound of formula (IV) or a salt thereof, or any stereoisomer or mixture thereof,

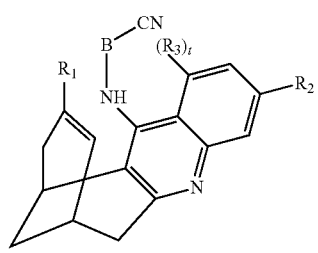

(IV)

wherein B is a birradical selected from the group consisting of —$(CH_2)_{n-1}$— and —$(CH_2)$— phenyl-, and n, $R_1$, $R_2$, $R_3$, and t are as defined in claim 1, respectively; to a reduction reaction to yield a compound of formula (III) or a salt thereof, or any stereoisomer or mixture thereof.

10. The process according to claim 9, further comprising a previous step of:
(a) reacting a compound of formula (V) or a salt thereof, or any stereoisomer or mixture thereof wherein $R_1$, $R_2$, $R_3$, and t are as defined in claim 1, respectively,

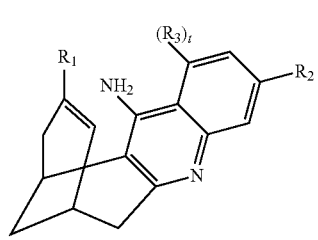

(V)

with a compound of formula (VI)

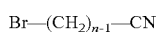

Br—$(CH_2)_{n-1}$—CN    (VI)

to yield a compound of formula (IV) wherein B is —$(CH_2)_{n-1}$— and n is as defined in claim 1, respectively; or alternatively, (a') with p-cyanobenzaldehyde to yield a compound of formula (IV'$_e$)

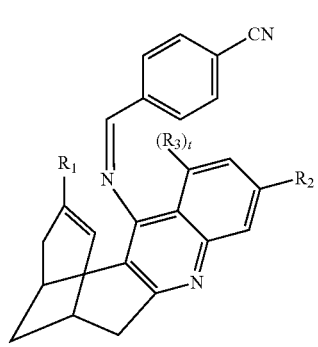

(IV'$_e$)

and then submitting the compound thus obtained to a reduction reaction to yield a compound of formula (IV) wherein B is —$(CH_2)$-phenyl-.

11. A method of treatment of Alzheimer's disease comprising administering a therapeutically effective amount of the compound of formula (I) as defined in claim 1, together with pharmaceutically acceptable excipients or carriers in a mammal suffering from Alzheimer's disease.

12. A pharmaceutical composition comprising a therapeutically effective amount of a compound as defined in claim 1, together with appropriate amounts of one or more pharmaceutically acceptable excipients or carriers.

13. A compound of formula (III) or a salt thereof, or any stereoisomer or mixture thereof,

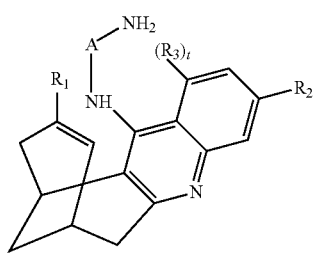
(III)

wherein:

$R_1$ is a ($C_1$-$C_2$) alkyl radical;

$R_2$ and $R_3$ are radicals independently selected from the group consisting of F, Cl, and methyl;

A is a birradical selected from the group consisting of —$(CH_2)_n$— and —$(CH_2)$-phenyl-$(CH_2)$—;

t is an integer from 0 to 1; and n is an integer from 8 to 15.

14. A compound selected from the group consisting of:

a compound of formula (IV) or a salt thereof, or any stereoisomer or mixture thereof,

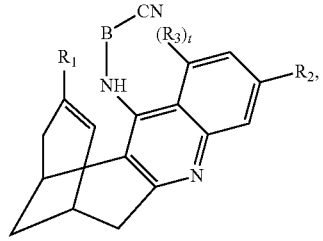
(IV)

or a compound of formula (IV'$_e$),

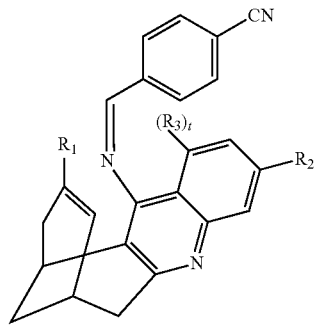
(IV'$_e$)

wherein:

$R_1$ is a ($C_1$-$C_2$) alkyl radical;

$R_2$ and $R_3$ are radicals independently selected from the group consisting of F, Cl, and methyl;

t is an integer from 0 to 1;

B is a birradical selected from the group consisting of —$(CH_2)_{n-1}$— and —$(CH_2)$-phenyl-, and n is an integer from 8 to 15.

15. A method according to claim 11 wherein the mammal is a human.

* * * * *